US012667625B2

(12) United States Patent
Launay et al.

(10) Patent No.: US 12,667,625 B2
(45) Date of Patent: Jun. 30, 2026

(54) ANTIBODY-DRUG CONJUCATES AND THEIR USES FOR THE TREATMENT OF CANCER

(71) Applicant: INATHERYS, Evry Cedex (FR)

(72) Inventors: Pierre Launay, Rueil Malmaison (FR); Hervé Souchet, Paris (FR); Coralie Belanger, Paris (FR)

(73) Assignee: INATHERYS, Evry Cedex (FR)

( * ) Notice: Subject to any disclaimer, the term of this patent is extended or adjusted under 35 U.S.C. 154(b) by 830 days.

(21) Appl. No.: 17/046,583

(22) PCT Filed: Apr. 9, 2019

(86) PCT No.: PCT/EP2019/058999
§ 371 (c)(1),
(2) Date: Oct. 9, 2020

(87) PCT Pub. No.: WO2019/197428
PCT Pub. Date: Oct. 17, 2019

(65) Prior Publication Data

US 2021/0138083 A1 May 13, 2021

(30) Foreign Application Priority Data

Apr. 10, 2018 (EP) .................................... 18305427

(51) Int. Cl.

| | |
|---|---|
| ***A61K 47/68*** | (2017.01) |
| ***A61K 47/22*** | (2006.01) |
| ***A61K 47/26*** | (2006.01) |
| ***A61P 35/00*** | (2006.01) |
| ***C07K 16/28*** | (2006.01) |

(52) U.S. Cl.
CPC .......... *A61K 47/6851* (2017.08); *A61K 47/22* (2013.01); *A61K 47/26* (2013.01); *A61K 47/68031* (2023.08); *A61K 47/6849* (2017.08); *A61K 47/6889* (2017.08); *A61P 35/00* (2018.01); *C07K 16/2881* (2013.01); *C07K 2317/76* (2013.01); *C07K 2317/92* (2013.01)

(58) Field of Classification Search
CPC .... A61K 47/6889; A61K 47/22; A61K 47/26; A61K 47/6803; A61K 47/6849; A61K 47/6851; A61K 47/65; A61K 38/05; A61P 35/00; A61P 35/02; C07K 16/2881; C07K 2317/76; C07K 2317/92
See application file for complete search history.

(56) References Cited

U.S. PATENT DOCUMENTS

| | | | | |
|---|---|---|---|---|
| 11,230,605 B2 * | 1/2022 | Launay | ................... | A61P 35/00 |
| 11,666,657 B2 * | 6/2023 | Wagner | ................... | A61P 35/00 424/181.1 |

FOREIGN PATENT DOCUMENTS

| | | | | |
|---|---|---|---|---|
| JP | 2013 158294 A | 8/2013 | | |
| WO | 03/026577 A2 | 4/2003 | | |
| WO | 2015/001117 A1 | 1/2015 | | |
| WO | WO-2017013230 A1 * | 1/2017 | ........... | A61K 39/395 |
| WO | 2019/008164 A1 | 1/2019 | | |

OTHER PUBLICATIONS

Tian, et al., J Pharm Sci 2014: 103:1701 (Year: 2014).*
Feng, et al., Cancer Cell International 2023 23:185 (Year: 2023).*
Chan, et al., PLoS ONE 2015 10(4) Article ID e0124708 (Year: 2015).*
Patil et al.; Temozolomide delivery to tumor cells by a multifunctional nano vehicle based on poly([beta]-L-malic acid); Pharmaceutical Research, vol. 27, No. 11, Nov. 1, 2010, pp. 2317-2329.

* cited by examiner

*Primary Examiner* — Julie Wu
*Assistant Examiner* — Sydney Van Druff
(74) *Attorney, Agent, or Firm* — WCF IP

(57) ABSTRACT

The present invention relates to antibody-drug conjugates, wherein the antibody specifically binds to TfR, the transferrin receptor, and wherein the drug is preferably chosen among a cytotoxic drug. Such antibody-drug conjugates are useful in particular in treating proliferative diseases including cancers, such as lymphoma or leukaemia.

18 Claims, 10 Drawing Sheets

Specification includes a Sequence Listing.

Histological examination of each organ depicted in Figures 6A and 6B is mentioned in Table 7.

SEQUENCE LISTING

```
<160> NUMBER OF SEQ ID NOS: 20

<210> SEQ ID NO 1
<211> LENGTH: 7
<212> TYPE: PRT
<213> ORGANISM: Homo sapiens

<400> SEQUENCE: 1

Gly Tyr Thr Phe Thr Asn Gln
1               5


<210> SEQ ID NO 2
<211> LENGTH: 6
<212> TYPE: PRT
<213> ORGANISM: Homo sapiens

<400> SEQUENCE: 2

Asn Thr Tyr Thr Gly Glu
1               5


<210> SEQ ID NO 3
<211> LENGTH: 8
<212> TYPE: PRT
<213> ORGANISM: Homo sapiens

<400> SEQUENCE: 3

Glu Gly Trp Asp Ser Met Asp Tyr
1               5


<210> SEQ ID NO 4
<211> LENGTH: 10
<212> TYPE: PRT
<213> ORGANISM: Homo sapiens

<400> SEQUENCE: 4

Ser Ala Ser Ser Ser Val Asn Tyr Met His
1               5                   10


<210> SEQ ID NO 5
<211> LENGTH: 7
<212> TYPE: PRT
<213> ORGANISM: Homo sapiens

<400> SEQUENCE: 5

Ser Thr Ser Asn Arg Ala Thr
1               5
```

<210> SEQ ID NO 6
<211> LENGTH: 9
<212> TYPE: PRT
<213> ORGANISM: Homo sapiens

<400> SEQUENCE: 6

```
Gln Gln Arg Ser Ser Tyr Pro Leu Thr
1               5
```

<210> SEQ ID NO 7
<211> LENGTH: 7
<212> TYPE: PRT
<213> ORGANISM: Homo sapiens

<400> SEQUENCE: 7

```
Ser Thr Ser Asn Leu Ala Ser
1               5
```

<210> SEQ ID NO 8
<211> LENGTH: 7
<212> TYPE: PRT
<213> ORGANISM: Homo sapiens

<400> SEQUENCE: 8

```
Ser Thr Ser Asn Arg Ala Ser
1               5
```

<210> SEQ ID NO 9
<211> LENGTH: 117
<212> TYPE: PRT
<213> ORGANISM: Homo sapiens

<400> SEQUENCE: 9

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Gln
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Ile Asn Ala Asp Asp Phe
    50                  55                  60

Lys Gly Arg Phe Ala Ile Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Val Arg Glu Gly Trp Asp Ser Met Asp Tyr Trp Gly Gln Gly Thr Ser
            100                 105                 110

Val Thr Val Ser Ser
        115
```

<210> SEQ ID NO 10
<211> LENGTH: 107
<212> TYPE: PRT
<213> ORGANISM: Homo sapiens

<400> SEQUENCE: 10

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Asn Tyr Met
            20                  25                  30
```

His Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ser Tyr Pro Leu Thr
85 90 95

Phe Gly Ala Gly Thr Lys Leu Glu Leu Lys Arg
100 105

<210> SEQ ID NO 11
<211> LENGTH: 117
<212> TYPE: PRT
<213> ORGANISM: Homo sapiens

<400> SEQUENCE: 11

Gln Val Gln Leu Val Gln Ser Gly Pro Glu Leu Lys Lys Pro Gly Ala
1 5 10 15

Ser Val Lys Val Ser Cys Lys Ala Ser Gly Tyr Thr Phe Thr Asn Gln
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Ile Asn Ala Asp Asp Phe
50 55 60

Lys Gly Arg Phe Val Ile Ser Leu Asp Thr Ser Ala Ser Thr Ala Tyr
65 70 75 80

Leu Gln Ile Ser Ser Leu Lys Ala Glu Asp Thr Ala Val Tyr Phe Cys
85 90 95

Val Arg Glu Gly Trp Asp Ser Met Asp Tyr Trp Gly Gln Gly Thr Ser
100 105 110

Val Thr Val Ser Ser
115

<210> SEQ ID NO 12
<211> LENGTH: 136
<212> TYPE: PRT
<213> ORGANISM: Homo sapiens

<400> SEQUENCE: 12

Met Glu Trp Ser Trp Val Phe Leu Phe Phe Leu Ser Val Thr Thr Gly
1 5 10 15

Val His Ser Gln Val Gln Leu Val Gln Ser Gly Pro Glu Leu Lys Lys
20 25 30

Pro Gly Ala Ser Val Lys Val Ser Cys Lys Ala Ser Gly Tyr Thr Phe
35 40 45

Thr Asn Gln Gly Met Asn Trp Val Lys Gln Ala Pro Gly Lys Gly Leu
50 55 60

Lys Trp Met Gly Trp Ile Asn Thr Tyr Thr Gly Glu Pro Ile Asn Ala
65 70 75 80

Asp Asp Phe Lys Gly Arg Phe Val Ile Ser Leu Glu Thr Ser Ala Ser
85 90 95

Thr Ala Tyr Leu Gln Ile Ser Asn Leu Lys Asn Glu Asp Thr Ala Val
100 105 110

Tyr Phe Cys Val Arg Glu Gly Trp Asp Ser Met Asp Tyr Trp Gly Gln
115 120 125

-continued

```
Gly Thr Ser Val Thr Val Ser Ser
    130                 135


<210> SEQ ID NO 13
<211> LENGTH: 107
<212> TYPE: PRT
<213> ORGANISM: Homo sapiens

<400> SEQUENCE: 13

Gln Ile Val Leu Thr Gln Ser Pro Ala Thr Leu Ser Val Ser Pro Gly
1               5                   10                  15

Glu Arg Ala Thr Leu Ser Cys Ser Ala Ser Ser Ser Val Asn Tyr Met
            20                  25                  30

His Trp Phe Gln Gln Lys Pro Gly Gln Ser Pro Arg Leu Leu Ile Tyr
        35                  40                  45

Ser Thr Ser Asn Arg Ala Thr Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gln Gly Thr Lys Leu Glu Ile Lys Arg
            100                 105


<210> SEQ ID NO 14
<211> LENGTH: 107
<212> TYPE: PRT
<213> ORGANISM: Homo sapiens

<400> SEQUENCE: 14

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Asn Tyr Met
            20                  25                  30

His Trp Phe Gln Gln Lys Pro Gly Gln Ser Pro Arg Leu Leu Ile Tyr
        35                  40                  45

Ser Thr Ser Asn Arg Ala Ser Gly Val Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Arg Ser Ser Tyr Pro Leu Thr
                85                  90                  95

Phe Gly Gln Gly Thr Lys Leu Glu Ile Lys Arg
            100                 105


<210> SEQ ID NO 15
<211> LENGTH: 107
<212> TYPE: PRT
<213> ORGANISM: Homo sapiens

<400> SEQUENCE: 15

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Asn Tyr Met
            20                  25                  30

His Trp Phe Gln Gln Lys Pro Gly Gln Ser Pro Arg Leu Leu Ile Tyr
        35                  40                  45

Ser Thr Ser Asn Leu Ala Ser Gly Val Pro Ala Arg Phe Ser Gly Ser
```

-continued

```
    50                  55                  60

Gly Ser Gly Thr Ser Tyr Thr Leu Thr Ile Ser Arg Leu Glu Pro Glu
65                  70                  75                  80

Asp Ala Ala Val Tyr Tyr Cys Gln Gln Arg Ser Ser Tyr Pro Leu Thr
                85                  90                  95

Phe Gly Ala Gly Thr Lys Leu Glu Leu Lys Arg
            100                 105


<210> SEQ ID NO 16
<211> LENGTH: 760
<212> TYPE: PRT
<213> ORGANISM: Homo sapiens

<400> SEQUENCE: 16

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320
```

-continued

```
Phe Pro Pro Ser Arg Ser Ser Gly Leu Pro Asn Ile Pro Val Gln Thr
            325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
```

```
        740                 745                 750

Val Trp Asp Ile Asp Asn Glu Phe
        755                 760


<210> SEQ ID NO 17
<211> LENGTH: 233
<212> TYPE: PRT
<213> ORGANISM: Homo sapiens

<400> SEQUENCE: 17

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
            20                  25                  30

Val Ser Pro Gly Glu Arg Ala Thr Leu Ser Cys Ser Ala Ser Ser Ser
        35                  40                  45

Val Asn Tyr Met His Trp Phe Gln Gln Lys Pro Gly Gln Ser Pro Arg
    50                  55                  60

Leu Leu Ile Tyr Ser Thr Ser Asn Arg Ala Thr Gly Ile Pro Ala Arg
65                  70                  75                  80

Phe Ser Gly Ser Gly Ser Gly Thr Ser Tyr Thr Leu Thr Ile Ser Ser
                85                  90                  95

Leu Glu Pro Glu Asp Phe Ala Val Tyr Tyr Cys Gln Gln Arg Ser Ser
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 18
<211> LENGTH: 462
<212> TYPE: PRT
<213> ORGANISM: Homo sapiens

<400> SEQUENCE: 18

Met Glu Trp Ser Trp Val Phe Leu Phe Phe Leu Ser Val Thr Thr Gly
1               5                   10                  15

Val His Ser Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Gln Gly Met Asn Trp Val Lys Gln Ala Pro Gly Lys Gly Leu
    50                  55                  60

Lys Trp Met Gly Trp Ile Asn Thr Tyr Thr Gly Glu Pro Ile Asn Ala
```

-continued

```
65                  70                  75                  80

Asp Asp Phe Lys Gly Arg Phe Val Ile Ser Leu Asp Thr Ser Ala Ser
                85                  90                  95

Thr Ala Tyr Leu Gln Ile Ser Ser Leu Lys Ala Glu Asp Thr Ala Val
            100                 105                 110

Tyr Phe Cys Val Arg Glu Gly Trp Asp Ser Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly
    450                 455                 460
```

<210> SEQ ID NO 19
<211> LENGTH: 724
<212> TYPE: DNA
<213> ORGANISM: Homo sapiens

<400> SEQUENCE: 19
aagcttgccg ccaccatgtc cgtgcctacc caggtgctgg gactgctgct gctgtggctg 60
accgatgcca ggtgccagat cgtgctgacc cagtctcctg ccaccctgtc tgtgtctccc 120
ggcgagagag ctaccctgtc ctgctccgcc tcctcctccg tgaactacat gcactggttc 180
cagcagaagc ccggccagtc ccccagactg ctgatctact ccacctccaa ccgggccacc 240
ggcatccctg ccagattttc cggctctggc tccggcacct cctataccct gaccatctcc 300
agcctggaac ccgaggactt cgccgtgtac tactgccagc agcggtcctc ctacccccctg 360 acctttggcc agggcaccaa gctggaaatc aagcgtacgg tggccgctcc cagcgtgttc 420
atcttccccc caagcgacga gcagctgaag agcggcaccg ccagcgtggt gtgtctgctg 480
aacaacttct accccaggga ggccaaggtg cagtggaagg tggacaacgc cctgcagagc 540
ggcaacagcc aggagagcgt caccgagcag gacagcaagg actccaccta cagcctgagc 600
agcaccctga ccctgagcaa ggccgactac gagaagcaca aggtgtacgc ctgtgaggtg 660
acccaccagg gcctgtccag ccccgtgacc aagagcttca acaggggcga gtgctgatga 720
attc 724

<210> SEQ ID NO 20
<211> LENGTH: 1411
<212> TYPE: DNA
<213> ORGANISM: Homo sapiens

<400> SEQUENCE: 20
aagcttgccg ccaccatgga atggtcctgg gtgttcctgt tcttcctgtc cgtgaccacc 60
ggcgtgcact cccaggtgca gctggtgcag tctggccccg agctgaagaa acctggcgcc 120
tccgtgaagg tgtcctgcaa ggcttccggc tacaccttta caaaccaggg catgaactgg 180
gtcaagcagg cccctggcaa gggcctgaag tggatgggct ggatcaacac ctacaccggc 240
gagcccatca acgccgacga cttcaagggc agattcgtga tctccctgga cacctccgcc 300
tccaccgcct acctgcagat cagctctctg aaggccgagg ataccgccgt gtacttctgc 360
gtgcgggaag gctgggactc catggactat tggggccagg gcacctccgt gaccgtgtct 420
agcgcttcta caaagggccc aagcgtgttc cccctggccc cctgctccag aagcaccagc 480
gagagcacag ccgccctggg ctgcctggtg aaggactact tccccgagcc cgtgaccgtg 540
tcctggaaca gcggagccct gaccagcggc gtgcacacct tccccgccgt gctgcagagc 600
agcggcctgt acagcctgag cagcgtggtg accgtgccca gcagcagcct gggcaccaag 660
acctacacct gtaacgtgga ccacaagccc agcaacacca aggtggacaa gagggtggag 720
agcaagtacg gcccaccctg ccccccctgc ccagcccccg agttcctggg cggacccagc 780
gtgttcctgt tcccccccaa gcccaaggac accctgatga tcagcagaac ccccgaggtg 840
acctgtgtgg tggtggacgt gtcccaggag gaccccgagg tccagttcaa ctggtacgtg 900
gacggcgtgg aggtgcacaa cgccaagacc aagcccagag aggagcagtt taacagcacc 960
taccgggtgg tgtccgtgct gaccgtgctg caccaggact ggctgaacgg caaagagtac 1020
aagtgtaagg tctccaacaa gggcctgcca agcagcatcg aaaagaccat cagcaaggcc 1080
aagggccagc ctagagagcc ccaggtctac accctgccac ccagccaaga ggagatgacc 1140
aagaaccagg tgtccctgac ctgtctggtg aagggcttct acccaagcga catcgccgtg 1200
gagtgggaga gcaacggcca gcccgagaac aactacaaga ccaccccccc agtgctggac 1260

-continued

| | |
|---|---|
| agcgacggca gcttcttcct gtacagcagg ctgaccgtgg acaagtccag atggcaggag | 1320 |
| ggcaacgtct ttagctgctc cgtgatgcac gaggccctgc acaaccacta cacccagaag | 1380 |
| agcctgagcc tgtccctggg ctgatgaatt c | 1411 |

ANTIBODY-DRUG CONJUCATES AND THEIR USES FOR THE TREATMENT OF CANCER

TECHNICAL FIELD

It is hereafter disclosed antibody-drug conjugates, wherein the antibody specifically binds to TfR, the transferrin receptor, and wherein the drug is preferably chosen among a cytotoxic drug. Such antibody-drug conjugates are useful in particular in treating proliferative diseases including cancers, such as lymphoma or leukaemia.

BACKGROUND

Antibody-drug conjugates (hereafter referred as "ADC") are a new class of therapeutics, notably cancer therapeutics. Such ADC comprise at least an antibody and a payload (e.g. a cytotoxic drug), both bonded by a linker. ADC are therefore designed to combine the specificity of antibody target with the efficiency of the payload (e.g. the cytotoxicity of a chemotherapeutic agent). Efficient ADC should exhibit high specificity and low toxicity.

Within the context of toxicity, antibody of ADC needs to bind accurately and efficiency to its antigen, meaning that the suitable target antigen is preferentially or exclusively expressed on target cells.

Several patents or patent applications, such as U.S. Pat. No. 6,214,345, WO 03/026577, WO 03/043583, WO 2004/010957, WO 2005/082023 and WO 2015/001117 disclose linkers that can be used for making ADC. Examples of linker types that have been used to conjugate a cytotoxin or a drug to an antibody include, but are not limited to, hydrazones, thioethers, esters, disulfides and peptide-containing linkers. Linkers are for example chosen among those susceptible to cleavage by low pH within the lysosomal compartment or susceptible to cleavage by proteases, such as proteases preferentially expressed in tumor tissue, for example cathepsins (e.g. cathepsins B, C, D). Efficient linker can ensure an accurate and timely release of the payload. Within the context of toxicity, it also appears that the stability of the linker can impact the toxicity exerted by the payload, even if the linker itself does not appear to drive toxicity. Indeed, a stable linker can release the payload in a target-specific manner whereas a not-stable linker is more likely to undergo a non-accurate release of the payload (for example due to a non-specific cleavage), leading to a non-specific toxicity.

Payloads used in ADC are highly potent, often cytotoxic drugs in the picomolar range. Common payloads are for example microtubule inhibitors (such as maytansine derivatives (DM1/DM4) or auristatins (MMAE/MMAF)), DNA synthesis inhibitors (such as calicheamicin, doxorubicin, pyrrolobenzodiazepines, indolinobenzodiazepines, or duocarmycin derivative), or topo-isomerase inhibitor (such as SN-38).

Although ADC appear to be promising therapeutics, some ADC can be too toxic, which limit the therapeutic window of these compounds or prevent further clinical development.

Efficient ADC exhibiting high specificity, maximum efficiency and low toxicity require therefore an appropriate combination of each of its components.

The transferrin receptor (CD71) (hereafter referred as "TfR") is a disulfide-linked homodimeric transmembrane glycoprotein consisting of two 760-amino acid monomers of approximately 90 kDa each. TfR plays a crucial role in the regulation of iron uptake and cell growth (Gill et al., N Engl J Med., 332, 1744-1748, 1995—Hermine et al., N Engl J Med., 332, 1749-1751, 1995). When diferric transferrin binds to its cell surface receptor, it is internalized via clathrin-coated pits to acidic vesicles where the iron-transferrin complex is dissociated. After release, the receptor and apo-transferrin recycle back to the cell surface.

TfR is constitutively expressed at the cell plasma membrane of tissues that are constantly renewed, such as precursors of blood cells in the bone marrow, hepatocytes in the liver, keratinocytes in the epidermis and enterocytes in crypts of intestinal epithelium.

Several studies have shown that TfR is expressed more abundantly in malignant tissues than in their healthy counterparts (Gatter et al., J Clin Pathol., 36, 539-545, 1983—Faulk et al., Lancet., 2,390-392, 1980—Shindelman et al., Int J Cancer, 27,329-334, 1981). Several authors have reported therapeutic approaches based on this idea using anti-TfR antibodies or transferrin itself conjugated to drugs to kill malignant cells. It has also been proposed to use anti-TfR antibodies to block the interaction between transferrin and TfR, and consequently preventing iron uptake, leading to iron deprivation and negative regulation of cell growth. However, although many publications describe the preparation of anti-TfR antibodies, there are very few reports of anti-TfR monoclonal antibodies (mAbs) having an antiproliferative activity.

In a previous publication (Moura et al., J Exp Med, 194, 417-425, 2001), the authors have reported a mouse monoclonal IgG (IgG2kappa), designated A24, that bind to the human TfR.

WO 2005/111082 discloses the A24 antibody, a murine antibody able to block T cell proliferation, and which appeared to be more efficient than the previously described mAb 42/6 in inhibiting proliferation of T cells. A24 also reduced TfR expression at the cell surface and impaired TfR recycling. A24 is also able to block the ex vivo proliferation of malignant T cells from both acute and chronic forms of ATL (Moura et al., *Blood,* 103,5, 1838-45,1 Mar. 2004, Callens et al., 2010; J. Exp. Med., Vol 207 No 4, pp 731-750). This antibody has been also described as able to prevent the mantle cell lymphoma tumor development both in vitro and in vivo (Lepelletier et al. *Cancer Res* 2007; 67:1145-1154; Callens et al. 2008, Leukemia, 22, 42-48).

WO 2017/013230 further discloses humanized versions of A24 antibodies, and their use in treating proliferative disorders. It also discloses an anti-TfR antibody conjugated to a therapeutic moiety, such as a cytotoxin or a drug. However, no specific ADC is disclosed in WO 2017/013230.

Therefore, there is a need for an ADC comprising an anti-TfR antibody which is efficient, which possess high specificity and low toxicity.

The inventors have thus developed such ADC. The present invention relies indeed on their unexpected results showing that ADC of the invention (i.e. comprising specific anti-TfR antibodies combined with specific linkers and drugs) possess the following advantages:

- A24 and ADC have similar binding efficacy on cells expressing TfR;
- ADC induce apoptosis of CD71 positive cells only;
- ADC are efficient on multiple cell lines;
- ADC are efficient in vitro, and also in vivo;
- ADC do not cause neither off-target effect (e.g. do not release pro-inflammatory cytokines) or toxic effect in vivo.

SUMMARY

The disclosure thus relates to ADC of the formula (I): Ab-L-Z—X-D, wherein:

Ab is an anti-TfR antibody,

L is a linker molecule bonded to said antibody, said linker molecule being of formula (II):

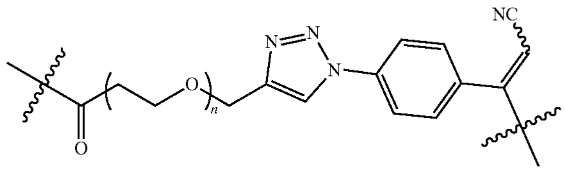

, wherein n is an integer comprised between 2 and 20,

Z is a dipeptide of valine-citrulline bonded to L,

X is an aminobenzyl ester self-immolative group bonded to Z,

D is a drug bonded to X.

In a specific embodiment, which can be combined with other embodiments, D is a cytotoxic drug. Preferably, such D is the drug monomethyl auristatin E (hereafter referred as "MMAE").

In a specific embodiment, which can be combined with other embodiments, X is a para-aminobenzyl ester group covalently bonded to Z, said X being of the following formula (III):

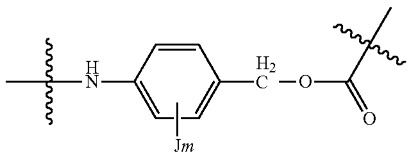

,

J being an optional substituent chosen among F, Cl, Br, $NO_2$, $NHCOCH_3$, $N(CH_3)_2$, $NHCOCF_3$, alkyl, and haloalkyl, and m being an integer of 0, 1, 2, 3 and 4. Preferably, X is a para-aminobenzyl ester wherein m is 0.

In a specific embodiment, which can be combined with other embodiments, L is covalently bonded to one or more thiol residues of said antibody. Preferably, L corresponds to a linker molecule of formula (IV):

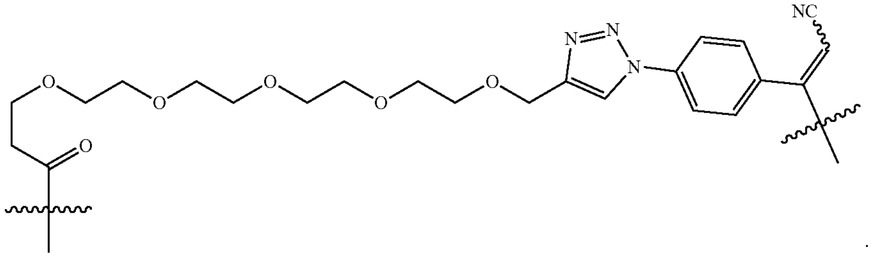 [SMILES: *C(=O)CCOCCOCCOCCOCCOCc1cn(-c2ccc(C(*)=CC#N)cc2)nn1]

.

In another specific embodiment, which can be combined with other embodiments, said antibody includes full-length antibodies or antibodies fragments containing antigen binding portions.

In another specific embodiment, which can be combined with other embodiments, said antibody specifically binds to the transferrin receptor of SEQ ID NO:16.

In another specific embodiment, which can be combined with other embodiments, said antibody binds to the transferrin receptor with a KD of 10 nM or less, preferably with a KD of 1 nM or less.

In another specific embodiment, which can be combined with other embodiments, said antibody induces apoptosis of HL-60 cell line to a level equal or superior to the induction level measured with the corresponding chimeric antibody with parental murine variable regions having VH of SEQ ID NO:9 and VL of SEQ ID NO:10.

In another specific embodiment, which can be combined with other embodiments, said antibody is a monoclonal antibody.

In another specific embodiment, which can be combined with other embodiments, said antibody is a humanized antibody.

In another specific embodiment, which can be combined with other embodiments, said antibody comprises a human IgG4 isotype constant region, or a mutant or chemically modified constant region, wherein said mutant or chemically modified constant region confers no or decreased ADCC activity to said antibody when compared to a corresponding antibody with wild type IgG1 isotype constant region. Alternatively, said antibody comprises a human IgG1 isotype constant region, or a mutant or chemically modified constant region, wherein said mutant or chemically modified constant region confers increased ADCC activity said antibody when compared to a corresponding antibody with wild type IgG1 isotype constant region.

In another specific and preferred embodiment, which can be combined with other embodiments, said anti-TfR antibody is a monoclonal and humanized antibody of IgG4 isotype.

In another specific and preferred embodiment, which can be combined with other embodiments, said anti-TfR antibody comprises either:

(a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6;

(b) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:8 and LCDR3 of SEQ ID NO:6;

(c) a variable heavy chain polypeptide comprising VH of SEQ ID NO:11 and a variable light chain polypeptide comprising VL of SEQ ID NO:13;

(d) a variable heavy chain polypeptide comprising VH of SEQ ID NO:11 and a variable light chain polypeptide comprising VL of SEQ ID NO:14;

(e) a variable heavy chain polypeptide comprising VH of SEQ ID NO:11 and a variable light chain polypeptide comprising VL of SEQ ID NO:15;

(f) a variable heavy chain polypeptide comprising VH of SEQ ID NO:12 and a variable light chain polypeptide comprising VL of SEQ ID NO:13;

(g) a variable heavy chain polypeptide comprising VH of SEQ ID NO:12 and a variable light chain polypeptide comprising VL of SEQ ID NO:14;

(h) a variable heavy chain polypeptide comprising VH of SEQ ID NO:12 and a variable light chain polypeptide comprising VL of SEQ ID NO:15.

Examples of antibodies that can be used in ADC of the invention include the humanized anti-TfR antibodies mAb1 to mAb16 as described below, in particular in Table 1. Preferably, said antibody is mAb1 comprising heavy chain of SEQ ID NO:18 and light chain of SEQ ID NO:17.

Also disclosed herein are ADC as defined above, for use as a medicament, notably for use in the treatment of cancer. Said cancer is preferably a hematologic tumor, and more specifically a lymphoma or leukaemia. Alternatively, said ADC may also be used in the treatment of a solid tumor.

The disclosure further relates to a pharmaceutical composition comprising an ADC as defined above, in combination with one or more pharmaceutical acceptable excipient, diluent or carrier, optionally comprising other active ingredients.

The disclosure further relates to a composition comprising an ADC as defined above, further comprising histidine, and having a pH of 6.5. Such composition can also comprise sucrose and polysorbate 80.

In a specific embodiment, said composition is a lyophilisate formulation, or said ADC is comprised in a pre-filled syringe or a pre-filled vial in a therapeutically acceptable amount.

The disclosure further relates to a process for obtaining an ADC as defined above, wherein the method comprises:

culturing a host cell under conditions suitable for expression of a nucleic acid encoding the antibody as defined above, isolating the antibody, synthesis of the monomethyl auristatin E bonded to the linker L-Z—X of formula (V):

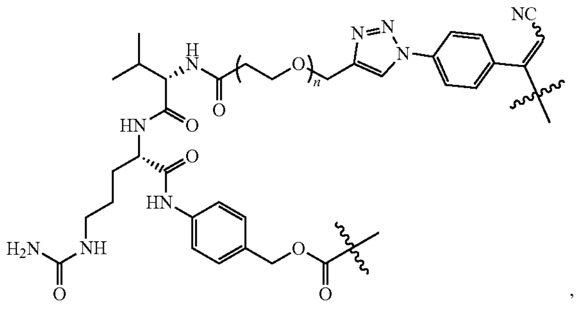

, conjugating said antibody to monomethyl auristatin E bonded to the linker L-Z—X of formula (V).

LEGENDS OF THE FIGURES

FIG. 2 represents comparative bindings of INA01-SDV1 and A24 on hematopoietic cell lines.

FIG. 3 represents the induction of programmed cell death (apoptosis) on CHO cell transfected or not with human CD71.

FIG. 4 represents in vitro efficacy by reduction of proliferation of INA01-SDV #1 on multiple cell-lines.

Figure 5:
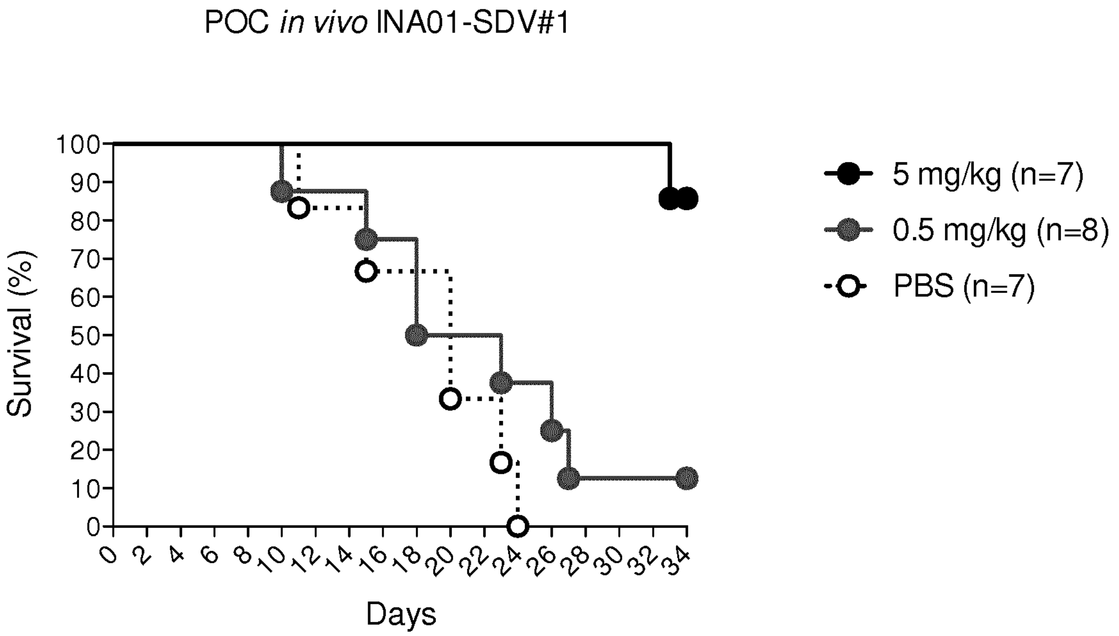

FIG. 5 represents in vivo efficacy of the INA01-SDV #1. FIG. 5 represents the Kaplan-Meier plot of the percentage of tumor-free mice xenografted with THP-1 cell line, after treatment. Treatment consists of only one administration of the ADC called INA01-SDV #1. Treatment is injected intraperitoneally (IP) when the tumor sizes were approximately 100 $mm^3$. Two dosages were tested (5 mg/kg and 0.5 mg/kg). n is the mouse number.

Figure 6A:
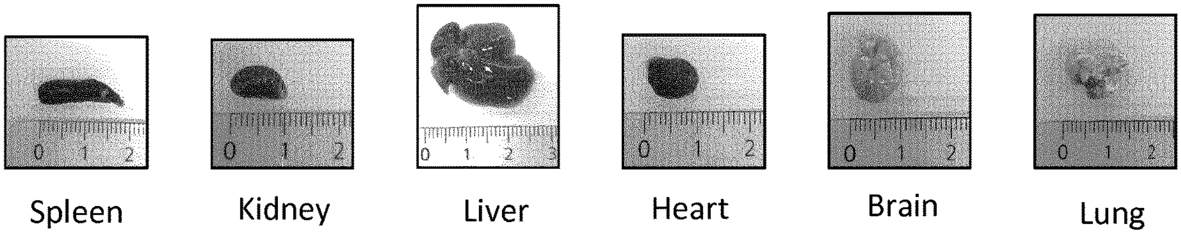
Figure 6B:
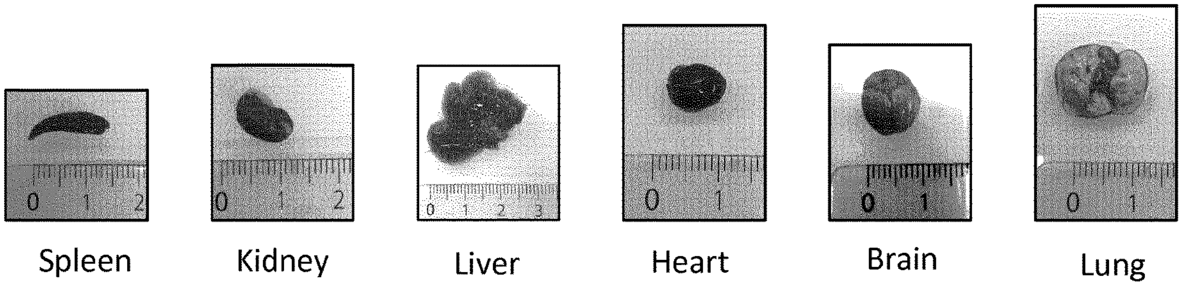

FIG. 6 represents the toxicology analysis of the INA01-SDV #1 in wild-type B6 (WT) mice and CD71/transferrin double knocking mice (TfR/Tf 2Ki) administered intraperitonealy at 3 mg/kg. Five injections every 4 days (q4dx5). FIG. 6A represents the macroscopic organ analysis in WT and FIG. 6B represents the macroscopic organ analysis in TfR/Tf 2Ki mice. Histological examination of each organ depicted in FIGS. 6A and 6B is mentioned in Table 7.

Figure 7:
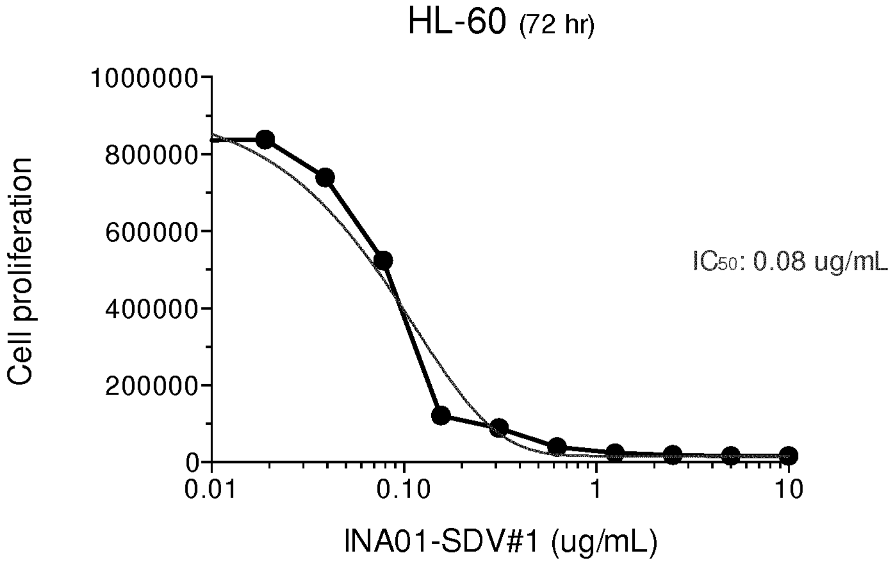

FIG. 7 represents the cell proliferation of HL-60 acute myeloid leukemia cell line, incubated during 72 hours at 37° C. with 10 concentrations of the ADC called INA01-SDV #1, ranging from 0.02 to 10 ug/mL. The fitted curve was used to calculate the $IC_{50}$ (0.08 ug/mL).

Figure 8:
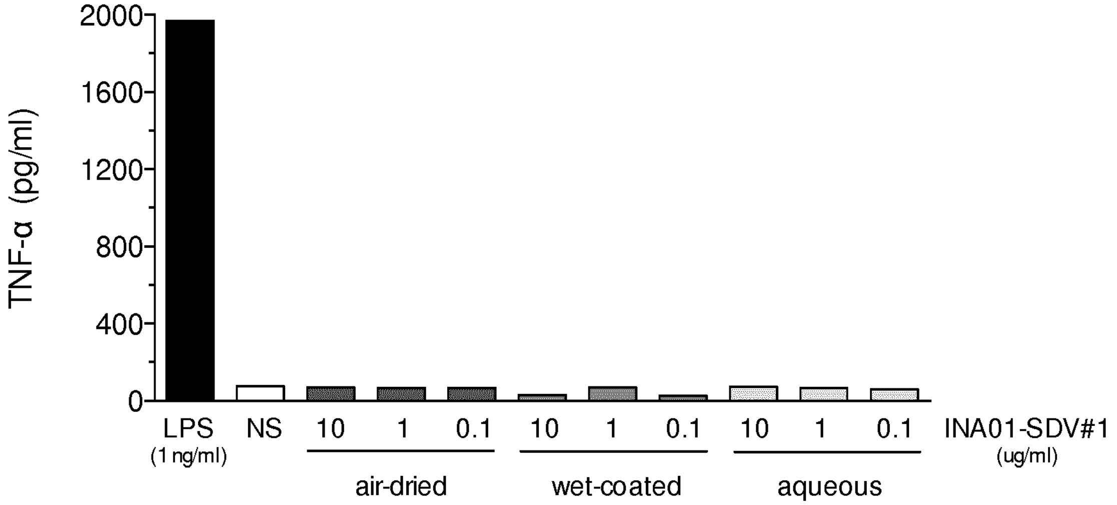

FIG. 8 represents the TNF-α production (in pg/mL) after incubation of PBMC (Peripheral Blood Mononuclear Cell) with the ADC called INA01-SDV #1 in three different conditions: high coated (air-dried), low coated (wet-coated) or in solution (aqueous). Three different concentrations of ADC were tested: 0.1, 1 and 10 ug/mL.

Figure 9:
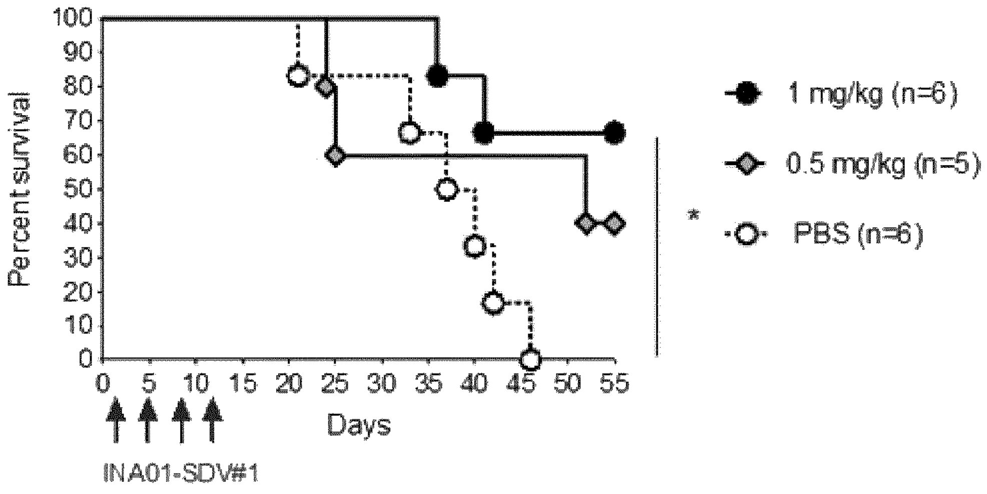

FIG. 9 represents in vivo efficacy of the INA01-SDV #1. FIG. 9 represents the Kaplan-Meier plot of the percentage of tumor-free mice xenografted with THP-1 cell line, after treatment. Treatment consists of 4 administrations, every 4 days, of the ADC called INA01-SDV #1. Treatment is injected intraperitoneally (IP) when the tumor sizes were approximately 100 $mm^3$. Two dosages were tested (1 mg/kg and 0.5 mg/kg). n is the mouse number. The p-value was determined using the log-rank test. *P=0.025.

Figure 10:
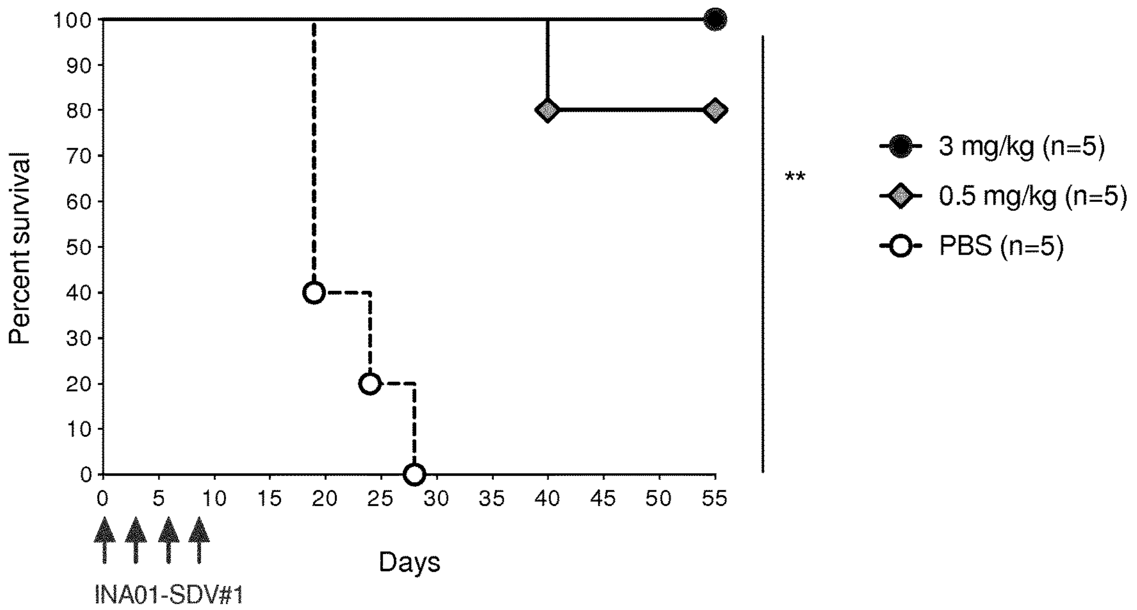

FIG. 10 represents in vivo efficacy of the INA01-SDV #1. FIG. 10 represents the Kaplan-Meier plot of the percentage of tumor-free mice xenografted with THP-1 cell line, after treatment. Treatment consists of 4 administrations, every 4 days, of the ADC called INA01-SDV #1. Treatment is injected intravenously (IV) when the tumor sizes were approximately 100 $mm^3$. Two dosages were tested (3 mg/kg and 0.5 mg/kg). n is the mouse number. The p-value was determined using the log-rank test. **P=0.0015.

DETAILED DESCRIPTION

Definitions

In order that the present disclosure may be more readily understood, certain terms are first defined. Additional definitions are set forth throughout the detailed description.

The term "CD71" or "transferrin receptor" or "TfR" refers to human TfR as defined in SEQ ID NO: 16, unless otherwise described. This sequence corresponds to Transferrin receptor protein 1 isoform 1 (*Homo sapiens*) (NCBI Reference Sequence NP_003225.2).

The term "antibody" as referred to herein includes whole antibodies and any antigen binding fragments (i.e. "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. The term "antigen-binding portion" of an antibody (or simply "antigen portion"), as used herein, refers to full length or one or more fragments of an antibody that retain the ability to specifically bind to an antigen (e.g. a portion of TfR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH domains; a $F(ab)_2$ fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a UniBody consisting of a single arm with a modified IgG heavy chain, for example IgG4, at the hinge region, a domain antibody fragment (Ward et al., 1989 Nature 341:544-546), or a nanobody fragment which consists of a VH domain; and an isolated complementarity determining region (CDR); or any fusion proteins comprising such antigen-binding portion. Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen binding portion" of an antibody. These antibody fragments are obtained using conventional techniques known to those of skill in the art, and the fragments are screened for utility in the same manner as are intact antibodies. An "isolated antibody", as used herein, refers to an antibody that is substantially free of other antibodies having different antigenic specificities (e.g. an isolated antibody that specifically binds to TfR is substantially free of antibodies that specifically bind to other antigens than TfR). An isolated antibody that specifically binds to TfR may, however, have cross-reactivity to other antigens, such as TfR molecules from other species. Moreover, an isolated antibody may be substantially free of other cellular material and/or chemicals. The phrases "an antibody recognizing an antigen" and "an antibody specific for an antigen" are used interchangeably herein with the term "an antibody which binds specifically to an antigen".

The terms "monoclonal antibody" or "monoclonal antibody composition" as used herein refers to a preparation of antibody molecules of single molecular composition. A monoclonal antibody composition displays a single binding specificity and affinity for a particular epitope.

As used herein, "isotype" refers to the antibody class (e.g. IgM, IgE, IgG such as IgG1 or IgG4) that is provided by the heavy chain constant region genes.

As used herein, an antibody or a protein that "specifically binds to an antigen", for example that "specifically binds to TfR" is intended to refer to an antibody or protein that binds to said antigen (for example human TfR of SEQ ID NO:16) with a KD of 100 nM or less, 10 nM or less, 1 nM or less.

The term "KD", as used herein, is intended to refer to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction.

As used herein, the term "affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity.

As used herein, the term "HL-60 cell line" refers to the promyelocytic derived by Collins et al. (PNAS 1978, 75:2458-1462) and also described in Gallagher et al. (Blood, 1979, 54:713-733), for example available at ATCC® collection under catalog number CCL-240™.

As used herein, the term "host cell" refers to prokaryotic or eukaryotic cells. Eukaryotic cells, for example mammalian host cells, yeast or filamentous fungi, are preferred, and in particular mammalian cells, because they are more likely than prokaryotic cells to assemble and secrete a properly folded and immunologically active antibody.

As used herein, the antibody "A24" refers to the antibody as disclosed in WO 2005/111082.

As used herein, the term "ADCC" or "antibody dependent cell cytotoxicity" activity refers to cell depleting activity. ADCC activity can be measured by ADCC assays commercially available, for example, ADCC Reporter Bioassay as commercialized by Promega under Ref #G7015.

As used herein, the term "apoptosis" refers to the programmed cell death. More information about apoptosis can be found in "Apoptosis: A Review of Programmed Cell Death, Susan Elmore, *Toxicol Pathol.* 2007; 35(4): 495-516.

As used herein, the term "$EC_{50}$" refers to the concentration of an antibody to induce a response, halfway between the baseline and maximum after a specified exposure time. For example, such concentration can be determined by GraphPad software.

As used herein, the term “subject” includes any human or nonhuman animal. The term “nonhuman animal” includes all vertebrates, e.g. mammals and non-mammals, such as nonhuman primates, sheep, dogs, cats, horses, cows, chickens, amphibians, reptiles, . . . . The term “subjects” also encompasses the term “patient”.

As used herein, the term “drug” also refers to “a payload”, i.e. a moiety that is conjugated to an antibody (or a fragment). D is not to be construed as limited to classical chemical therapeutic agent. For example, D can encompass a protein, a peptide or a polypeptide possessing a desired biological activity. Preferably, it refers to a therapeutic moiety, such as a cytotoxin. A “cytotoxin” or “cytotoxic agent” includes any agent that is detrimental to (e.g. kills) cells.

As used herein, the term “linker molecule” refers to compounds of formulas (II) or (IV). Such linker molecules are appropriate to be linked to a compound comprising a thiol moiety, such as an antibody.

As used herein, the term “dipeptide of valine-citrulline” (hereafter referred as “dipeptide VC”) represents a linker consisting of two amino acids valine and citrulline. This dipeptide is notably of formula (VI):

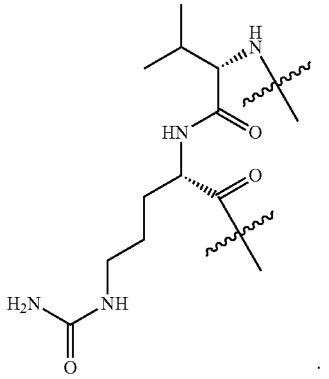 [SMILES: *N[C@H](C(=O)N[C@@H](CCCNC(N)=O)C(*)=O)C(C)C]

As used herein, the term “aminobenzyl ester self-immolative group” refers to an aminobenzyl ester group that functions as a self immolative group. Such group is represented by a compound of formula (III). A “self-immolative group” may be defined as a bifunctional chemical moiety which (i) is capable of covalently linking together at least two other chemical moieties into a stable molecule, (ii) can be released from one of the spaced chemical moieties from the molecule by means of enzymatic cleavage, and (iii) following enzymatic cleavage, can spontaneously cleave from the remainder of the molecule to release the other of the spaced chemical moieties.

As used herein, the term “alkyl” refers to a monovalent saturated hydrocarbon chain (having straight or branched chain). For example, alkyl refers to $C_1$-$C_{20}$ alkyl. Preferably, the alkyl is a “lower alkyl”, i.e. an alkyl group having 1, 2, 3, 4, 5 or 6 carbons (straight or branched chain $C_1$-$C_6$ alkyl group). For example, this includes methyl, ethyl, n-propyl, i-propyl, n-butyl, i-butyl, sec-butyl, tert-butyl, n-pentyl, n-hexyl, and the like.

As used herein, the term “haloalkyl” refers to an alkyl having one or more hydrogen atoms replaced by one or halogen atoms. Preferably, the haloalkyl is a “lower haloalkyl”, i.e. a haloalkyl group having 1, 2, 3, 4, 5 or 6 carbons (straight or branched chain $C_1$-$C_6$ haloalkyl group). For example, this includes $CF_3$, $CF_2Br$, $CH_2F$, $CHFCH_3$, $CF_3CH_2$, $CF_3CF_2$, $CHF_2CF_2$, $CH_2Cl$, or $CH_2CH_2Cl$.

As used herein, the term “bonded” refers to a linkage. This linkage is also represented by the dash “-” in formula (I). Linkage may be a covalent bond, or a non-covalent interaction such as through electrostatic forces. Preferably, bonds are covalent bonds. As used herein, the “wavy lines” on formulas represents the attachment sites between each part (Ab, L, Z, X and D) of the ADC of the disclosure.

As used herein “therapeutically acceptable amount” refers to an amount sufficient to effect the desired results (for example a reduction in tumor size, inhibition of tumor growth, prevention of metastasis, induction of apoptosis, . . . ).

Recombinant Antibodies

Antibodies of the disclosure are anti-TfR antibodies. Preferably, such antibodies include the humanized recombinant antibodies mAb1-mAb16, isolated and structurally characterized by their variable heavy and light chain amino acid sequences and human constant isotype as described in the Table 1 below:

TABLE 1

Variable heavy and light chain amino acid sequences of mAb1-mAb16

| Antibody | VH Amino acid sequence | VL Amino acid sequence | Isotype constant region |
|---|---|---|---|
| mAb1 | SEQ ID NO: 11 (VH4) | SEQ ID NO: 13_(VL4) | IgG4 |
| mAb2 | SEQ ID NO: 11 (VH4) | SEQ ID NO: 14 (VL5) | IgG4 |
| mAb3 | SEQ ID NO: 12 (VH5) | SEQ ID NO: 13 (VL4) | IgG4 |
| mAb4 | SEQ ID NO: 12 (VH5) | SEQ ID NO: 15 (VL6) | IgG4 |
| mAb5 | SEQ ID NO: 11 (VH4) | SEQ ID NO: 13_(VL4) | IgG1 |
| mAb6 | SEQ ID NO: 11 (VH4) | SEQ ID NO: 14 (VL5) | IgG1 |
| mAb7 | SEQ ID NO: 12 (VH5) | SEQ ID NO: 13 (VL4) | IgG1 |
| mAb8 | SEQ ID NO: 12 (VH5) | SEQ ID NO: 15 (VL6) | IgG1 |
| mAb9 | SEQ ID NO: 11 (VH4) | SEQ ID NO: 13_(VL4) | IgG1 (AA) |
| mAb10 | SEQ ID NO: 11 (VH4) | SEQ ID NO: 14 (VL5) | IgG1 (AA) |
| mAb11 | SEQ ID NO: 12 (VH5) | SEQ ID NO: 13 (VL4) | IgG1 (AA) |
| mAb12 | SEQ ID NO: 12 (VH5) | SEQ ID NO: 15 (VL6) | IgG1 (AA) |
| mAb13 | SEQ ID NO: 11 (VH4) | SEQ ID NO: 13_(VL4) | IgG1 N297A |
| mAb14 | SEQ ID NO: 11 (VH4) | SEQ ID NO: 14 (VL5) | IgG1 N297A |
| mAb15 | SEQ ID NO: 12 (VH5) | SEQ ID NO: 13 (VL4) | IgG1 N297A |
| mAb16 | SEQ ID NO: 12 (VH5) | SEQ ID NO: 15 (VL6) | IgG1 N297A |

The corresponding amino acid and nucleotide coding sequence of the constant isotype regions of IgG4, IgG1 and their mutant versions IgG1 AA and IgG1 N297A used for generating mAb1 to mAb16 are well-known in the art. Full length light and heavy chains and corresponding coding sequences of mAb1 is shown in the Table 2 below.

TABLE 2

Full length heavy and light chain DNA coding sequences

| Antibody | Amino acid sequence | DNA coding sequence |
|---|---|---|
| mAb1 | Heavy Chain: SEQ ID NO: 18 | Heavy Chain: SEQ ID NO: 20 |
| | Light Chain: SEQ ID NO: 17 | Light Chain: SEQ ID NO: 19 |

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of some antibodies according to the disclosure are shown in Table 3.

In Table 3, the CDR regions of some antibodies of the present disclosure are delineated using the Chothia system (Chothia C, Lesk A M. 1987, J Mol Biol 196, 901-917). For the ease of reading, the CDR regions are called hereafter HCDR1, HCDR2, HCDR3, LCDR1, LCDR2, LCDR3 respectively.

TABLE 3

CDR regions of mAb1 to mAb16 and reference A24 antibody according to Chothia

| Original antibody | HCDR1 | HCDR2 | HCDR3 | LCDR1 | LCDR2 | LCDR3 |
|---|---|---|---|---|---|---|
| A24 | SEQ ID NO: 1 | SEQ ID NO: 2 | SEQ ID NO: 3 | SEQ ID NO: 4 | SEQ ID NO: 7 | SEQ ID NO: 6 |
| mAb1<br>mAb5<br>mAb9<br>mAb13 | SEQ ID NO: 1 | SEQ ID NO: 2 | SEQ ID NO: 3 | SEQ ID NO: 4 | SEQ ID NO: 5 | SEQ ID NO: 6 |
| mAb2<br>mAb6<br>mAb10<br>mAb14 | SEQ ID NO: 1 | SEQ ID NO: 2 | SEQ ID NO: 3 | SEQ ID NO: 4 | SEQ ID NO: 8 | SEQ ID NO: 6 |

TABLE 3-continued

CDR regions of mAb1 to mAb16 and reference A24 antibody according to Chothia

| Original antibody | HCDR1 | HCDR2 | HCDR3 | LCDR1 | LCDR2 | LCDR3 |
|---|---|---|---|---|---|---|
| mAb3<br>mAb7<br>mAb11<br>mAb15 | SEQ ID NO: 1 | SEQ ID NO: 2 | SEQ ID NO: 3 | SEQ ID NO: 4 | SEQ ID NO: 5 | SEQ ID NO: 6 |
| mAb4<br>mAb8<br>mAb12<br>mAb16 | SEQ ID NO: 1 | SEQ ID NO: 2 | SEQ ID NO: 3 | SEQ ID NO: 4 | SEQ ID NO: 7 | SEQ ID NO: 6 |

Tables 4, 5 and 6 describe useful amino acid and nucleotides sequences relative to antibodies of ADC.

TABLE 4

Brief description of useful amino acid and nucleotide sequences for practicing the invention

| SEQ ID NO: | Description of the sequence |
|---|---|
| 1 | HCDR1 amino acid sequence of A24, VH4 and VHS |
| 2 | HCDR2 amino acid sequence of A24, VH4 and VHS |
| 3 | HCDR3 amino acid sequence of A24, VH4 and VHS |
| 4 | LCDR1 amino acid sequence of A24, VL4, VL5 and VL6 |
| 5 | LCDR2 amino acid sequence of VL4 |
| 6 | LCDR3 amino acid sequence of A24, VL4, VL5 and VL6 |
| 7 | LCDR2 amino acid sequence of A24 |
| 8 | LCDR2 amino acid sequence of VL5 |
| 9 | VH0 amino acid sequence of A24 |
| 10 | VL0 amino acid sequence of A24 |
| 11 | VH4 amino acid sequence |
| 12 | VH5 amino acid sequence |
| 13 | VL4 amino acid sequence |
| 14 | VL5 amino acid sequence |
| 15 | VL6 amino acid sequence |
| 16 | Human transferrin receptor amino acid sequence |
| 17 | Full length light chain of mAb1, mAb3, mAb5, mAb7, mAb9, mAb11, mAb13, mAb15 (with VL4) |
| 18 | Full length heavy chain of mAbl, mAb2 (with VH4-IgG4 isotype) |
| 19 | Nucleotide sequence encoding Full length light chain of mAb1, mAb3, mAb5, mAb7, mAb9, mAb11, mAb13, mAb15 (with VL4) of SEQ ID NO: 19 |
| 20 | Nucleotide sequence encoding Full length heavy chain of mAb1, mAb2 (with VH4-IgG4 isotype) of SEQ ID NO: 22 |

TABLE 5

Brief description of useful amino acid and nucleotide sequences for practicing the invention

| SEQ ID NO: | Describes the amino acid or nucleotide sequence below: |
|---|---|
| 1 | GYTFTNQ |
| 2 | NTYTGE |
| 3 | EGWDSMDY |
| 4 | SASSSVNYMH |
| 5 | STSNRAT |
| 6 | QQRSSYPLT |
| 7 | STSNLAS |
| 8 | STSNRAS |

TABLE 5-continued

Brief description of useful amino acid and nucleotide sequences for practicing the invention

| SEQ ID NO: | Describes the amino acid or nucleotide sequence below: |
|---|---|
| 9 | QIQLVQSGPELKKPGETVKISCKAS**GYTFTNQG**MNWVKQAPGKGLKWMGWI**N**<br>**TYTGE**PINADDFKGRFAISLETSASTAYLQINNLKNEDMATYFCVR**EGWDSMD**<br>**Y**WGQGTSVTVSS |
| 10 | QIVLTQSPAIMSASPGEKVTITC**SASSSVNYMH**WFQQKPGTSPKLWIY**STSNLAS**<br>GVPARFSGSGSGTSYSLTISRMEAEDAATYYC**QQRSSYPLT**FGAGTKLELKR |
| 11 | QVQLVQSGPELKKPGASVKVSCKASG**YTFTNQG**MNWVKQAPGKGLKWMGWI<br>**NTYTGE**PINADDFKGRFVISLDTSASTAYLQISSLKAEDTAVYFCVR**EGWDSMD**<br>**Y**WGQGTSVTVSS |
| 12 | MEWSWVFLFFLSVTTGVHSQVQLVQSGPELKKPGASVKVSCKAS**GYTFTNQG**<br>MNWVKQAPGKGLKWMGWI**NTYTGE**PINADDFKGRFVISLETSASTAYLQISNL<br>KNEDTAVYFCV**REGWDSMDY**WGQGTSVTVSS |
| 13 | QIVLTQSPATLSVSPGERATLSC**SASSSVNYMH**WFQQKPGQSPRLLIY**STSNRAT**<br>GIPARFSGSGSGTSYTLTISSLEPEDFAVYYC**QQRSSYPLT**FGQGTKLEIKR |
| 14 | QIVLTQSPATLSLSPGERATLSC**SASSSVNYMH**WFQQKPGQSPRLLIY**STSNRAS**<br>GVPARFSGSGSGTSYTLTISRLEPEDFAVYYC**QQRSSYPLT**FGQGTKLEIKR |
| 15 | QIVLTQSPATLSLSPGERATLSC**SASSSVNYMH**WFQQKPGQSPRLLIY**STSNLAS**<br>GVPARFSGSGSGTSYTLTISRLEPEDAAVYYC**QQRSSYPLT**FGAGTKLELKR |
| 16 | MMDQARSAFSNLFGGEPLSYTRFSLARQVDGDNSHVEMKLAVDEEENADNNT<br>KANVTKPKRCSGSICYGTIAVIVFFLIGFMIGYLGYCKGVEPKTECERLAGTESPV<br>REEPGEDFPAARRLYWDDLKRKLSEKLDSTDFTGTIKLLNENSYVPREAGSQKD<br>ENLALYVENQFREFKLSKVWRDQHFVKIQVKDSAQNSVIIVDKNGRLVYLVENP<br>GGYVAYSKAATVTGKLVHANFGTKKDFEDLYTPVNGSIVIVRAGKITFAEKVAN<br>AESLNAIGVLIYMDQTKFPIVNAELSFFGHAHLGTGDPYTPGFPSFNHTQFPPSRS<br>SGLPNIPVQTISRAAAEKLFGNMEGDCPSDWKTDSTCRMVTSESKNVKLTVSNV<br>LKEIKILNIFGVIKGFVEPDHYVVVGAQRDAWGPGAAKSGVGTALLLKLAQMFS<br>DMVLKDGFQPSRSIIFASWSAGDFGSVGATEWLEGYLSSLHLKAFTYINLDKAV<br>LGTSNFKVSASPLLYTLIEKTMQNVKHPVTGQFLYQDSNWASKVEKLTLDNAAF<br>PFLAYSGIPAVSFCFCEDTDYPYLGTTMDTYKELIERIPELNKVARAAAEVAGQF<br>VIKLTHDVELNLDYERYNSQLLSFVRDLNQYRADIKEMGLSLQWLYSARGDFFR<br>ATSRLTTDFGNAEKTDRFVMKKLNDRVMRVEYHFLSPYVSPKESPFRHVFWGS<br>GSHTLPALLENLKLRKQNNGAFNETLFRNQLALATWTIQGAANALSGDVWDID<br>NEF |
| 17 | MSVPTQVLGLLLLWLTDARCQIVLTQSPATLSVSPGERATLSCSASSSVNYMHW<br>FQQKPGQSPRLLIYSTSNRATGIPARFSGSGSGTSYTLTISSLEPEDFAVYYCQQRS<br>SYPLTFGQGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQG<br>LSSPVTKSFNRGEC |
| 18 | MEWSWVFLFFLSVTTGVHSQVQLVQSGPELKKPGASVKVSCKASGYTFTNQGM<br>NWVKQAPGKGLKWMGWINTYTGEPINADDFKGRFVISLDTSASTAYLQISSLKA<br>EDTAVYFCVREGWDSMDYWGQGTSVTVSSASTKGPSVFPLAPCSRSTSESTAAL<br>GCLVKDYFPEPVTVSWNSGALTSGVHTFPAVLQSSGLYSLSSVVYVPSSSLGTKT<br>YTCNVDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQ<br>VSLTCLVKGFYPSDIAVEWESNGQPENNYKTTPPVLDSDGSFFLYSRLTVDKSR<br>WQEGNVFSCSVMHEALHNHYTQKSLSLSLG |
| 19 | AAGCTTGCCGCCACCATGTCCGTGCCTACCCAGGTGCTGGGACTGCTGCTGC<br>TGTGGCTGACCGATGCCAGGTGCCAGATCGTGCTGACCCAGTCTCCTGCCAC<br>CCTGTCTGTGTCTCCCGGCGAGAGAGCTACCCTGTCCTGCTCCGCCTCCTCCT<br>CCGTGAACTACATGCACTGGTTCCAGCAGAAGCCCGGCCAGTCCCCCAGACT<br>GCTGATCTACTCCACCTCCAACCGGGCCACCGGCATCCCTGCCAGATTTTCCG<br>GCTCTGGCTCCGGCACCTCCTATACCCTGACCATCTCCAGCCTGGAACCCGA<br>GGACTTCGCCGTGTACTACTGCCAGCAGCGGTCCTCCTACCCCCTGACCTTTG<br>GCCAGGGCACCAAGCTGGAAATCAAGCGTACGGTGGCCGCTCCCAGCGTGTT<br>CATCTTCCCCCCAAGCGACGAGCAGCTGAAGAGCGGCACCGCCAGCGTGGTG<br>TGTCTGCTGAACAACTTCTACCCCAGGGAGGCCAAGGTGCAGTGGAAGGTGG<br>ACAACGCCCTGCAGAGCGGCAACAGCCAGGAGAGCGTCACCGAGCAGGACA<br>GCAAGGACTCCACCTACAGCCTGAGCAGCACCCTGACCCTGAGCAAGGCCG<br>ACTACGAGAAGCACAAGGTGTACGCCTGTGAGGTGACCCACCAGGGCCTGTC<br>CAGCCCCGTGACCAAGAGCTTCAACAGGGGCGAGTGCTGATGAATTC |

TABLE 5-continued

Brief description of useful amino acid and nucleotide sequences for practicing the invention

| SEQ ID NO: | Describes the amino acid or nucleotide sequence below: |
|---|---|
| 20 | AAGCTTGCCGCCACCATGGAATGGTCCTGGGTGTTCCTGTTCTTCCTGTCCGT<br>GACCACCGGCGTGCACTCCCAGGTGCAGCTGGTGCAGTCTGGCCCCGAGCTG<br>AAGAAACCTGGCGCCTCCGTGAAGGTGTCCTGCAAGGCTTCCGGCTACACCT<br>TTACAAACCAGGGCATGAACTGGGTCAAGCAGGCCCCTGGCAAGGGCCTGA<br>AGTGGATGGGCTGGATCAACACCTACACCGGCGAGCCCATCAACGCCGACG<br>ACTTCAAGGGCAGATTCGTGATCTCCCTGGACACCTCCGCCTCCACCGCCTAC<br>CTGCAGATCAGCTCTCTGAAGGCCGAGGATACCGCCGTGTACTTCTGCGTGC<br>GGGAAGGCTGGGACTCCATGGACTATTGGGGCCAGGGCACCTCCGTGACCGT<br>GTCTAGCGCTTCTACAAAGGGCCCAAGCGTGTTCCCCCTGGCCCCCTGCTCCA<br>GAAGCACCAGCGAGAGCACAGCCGCCCTGGGCTGCCTGGTGAAGGACTACT<br>TCCCCCGAGCCCGTGACCGTGTCCTGGAACAGCGGAGCCCTGACCAGCGGCGT<br>GCACACCTTCCCCGCCGTGCTGCAGAGCAGCGGCCTGTACAGCCTGAGCAGC<br>GTGGTGACCGTGCCCAGCAGCAGCCTGGGCACCAAGACCTACACCTGTAACG<br>TGGACCACAAGCCCAGCAACACCAAGGTGGACAAGAGGGTGGAGAGCAAGT<br>ACGGCCCACCCTGCCCCCCCTGCCCAGCCCCCGAGTTCCTGGGCGGACCCAG<br>CGTGTTCCTGTTCCCCCCCAAGCCCAAGGACACCCTGATGATCAGCAGAACC<br>CCCGAGGTGACCTGTGTGGTGGTGGACGTGTCCCAGGAGGACCCCGAGGTCC<br>AGTTCAACTGGTACGTGGACGGCGTGGAGGTGCACAACGCCAAGACCAAGC<br>CCAGAGAGGAGCAGTTTAACAGCACCTACCGGGTGGTGTCCGTGCTGACCGT<br>GCTGCACCAGGACTGGCTGAACGGCAAAGAGTACAAGTGTAAGGTCTCCAA<br>CAAGGGCCTGCCAAGCAGCATCGAAAAGACCATCAGCAAGGCCAAGGGCCA<br>GCCTAGAGAGCCCCAGGTCTACACCCTGCCACCCAGCCAAGAGGAGATGAC<br>CAAGAACCAGGTGTCCCTGACCTGTCTGGTGAAGGGCTTCTACCCAAGCGAC<br>ATCGCCGTGGAGTGGGAGAGCAACGGCCAGCCCGAGAACAACTACAAGACC<br>ACCCCCCCAGTGCTGGACAGCGACGGCAGCTTCTTCCTGTACAGCAGGCTGA<br>CCGTGGACAAGTCCAGATGGCAGGAGGGCAACGTCTTTAGCTGCTCCGTGAT<br>GCACGAGGCCCTGCACAACCACTACACCCAGAAGAGCCTGAGCCTGTCCCTG<br>GGCTGATGAATTC |

TABLE 6

Description of the variable regions and IgG Fc region of mAb1-mAb16

| Example | Variable region and IgG Fc region |
|---|---|
| mAb1 | VH4/VL4 with IgG4 Fc region |
| mAb2 | VH4/VL5 with IgG4 Fc region |
| mAb3 | VH5/VL4 with IgG4 Fc region |
| mAb4 | VH5/VL6 with IgG4 Fc region |
| mAb5 | VH4/VL4 with IgG1 Fc region |
| mAb6 | VH4/VL5 with IgG1 Fc region |
| mAb7 | VH5/VL4 with IgG1 Fc region |
| mAb8 | VH5/VL6 with IgG1 Fc region |
| mAb9 | VH4/VL4 with IgG1 AlaAla mutant Fc region |
| mAb10 | VH4/VL5 with IgG1 AlaAla mutant Fc region |
| mAb11 | VH5/VL4 with IgG1 AlaAla mutant Fc region |
| mAb12 | VH5/VL6 with IgG1 AlaAla mutant Fc region |
| mAb13 | VH4/VL4 with IgG1 N297A mutant Fc region |
| mAb14 | VH4/VL5 with IgG1 N297A mutant Fc region |
| mAb15 | VH5/VL4 with IgG1 N297A mutant Fc region |
| mAb16 | VH5/VL6 with IgG1 N297A mutant Fc region |

In one embodiment, an isolated recombinant antibody has: a heavy chain variable region comprising HCDR1 of SEQ ID NO: 1; HCDR2 of SEQ ID NO: 2; HCDR3 of SEQ ID NO: 3; a light chain variable region comprising LCDR1 of SEQ ID NO: 4; LCDR2 of SEQ ID NOs: 5 or 8; and LCDR3 of SEQ ID NOs: 6; wherein said antibody specifically binds to the transferrin receptor of SEQ ID NO:16.

In specific embodiments, the isolated recombinant antibody according to the disclosure comprises either:

(a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6;

(b) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:8 and LCDR3 of SEQ ID NO:6;

(c) a variable heavy chain polypeptide comprising VH of SEQ ID NO:11 and a variable light chain polypeptide VL of SEQ ID NO:13;

(d) a variable heavy chain polypeptide comprising VH of SEQ ID NO:11 and a variable light chain polypeptide VL of SEQ ID NO:14;

(e) a variable heavy chain polypeptide comprising VH of SEQ ID NO:11 and a variable light chain polypeptide VL of SEQ ID NO:15;

(f) a variable heavy chain polypeptide comprising VH of SEQ ID NO:12 and a variable light chain polypeptide VL of SEQ ID NO:13;

(g) a variable heavy chain polypeptide comprising VH of SEQ ID NO:12 and a variable light chain polypeptide VL of SEQ ID NO:14; or (h) a variable heavy chain polypeptide comprising VH of SEQ ID NO:12 and a variable light chain polypeptide VL of SEQ ID NO:15.

In a specific embodiment, said recombinant anti-TfR antibody as defined above have one or more of the following properties:

(i) it binds to the transferrin receptor with a KD of 10 nM or less, preferably with a KD of 1 nM or less, as measured by SPR;

(ii) it binds to the transferrin receptor with an $EC_{50}$ of 0.1 μg/ml or below, preferably of 0.05 μg/ml or below, as measured in an ELISA assay (see PCT/EP2016/067465 for more information);

(iii) it induces apoptosis of HL-60 cell line to a level equal or superior to the induction level measured with the corresponding reference chimeric antibody having the parental murine variable regions with VH of SEQ ID NO:9 and VL of SEQ ID NO:10, for example as measured using the HL-60 apoptosis induction assay. Typically, an amount of 10 g/ml of a recombinant antibody of the present disclosure may be assayed for induction of apoptosis of HL-60 cell line as compared to the same amount of the reference chimeric antibody with the parental murine variable regions of A24 comprising VH of SEQ ID NO:9 and VL of SEQ ID NO:10. Induction of apoptosis in the HL-60 apoptosis induction assay of a tested antibody is equal to a reference antibody if the percentage of positive cells as measured with the tested antibody is not significantly lower that the percentage of positive cells as measured with the reference antibody.

As used herein, a "corresponding" reference chimeric antibody refers to the reference antibody with an isotype constant region 100% identical to the isotype constant region of the antibody to be tested for a particular property, for example induction of apoptosis.

In certain embodiments that may be combined with the previous embodiments, an antibody provided herein is an antibody fragment of the above-defined antibodies. Antibody fragments include, but are not limited to, Fab, Fab', Fab'-SH, $F(ab')_2$, Fv, UniBody, and scFv fragments, diabodies, single domain or nanobodies and other fragments. The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1). Antibody fragments can be made by various techniques, including but not limited to proteolytic digestion of an intact antibody as well as production by recombinant host cells as described herein.

In certain embodiments, the antibody of the present disclosure is a humanized antibody. Typically, a non-human antibody is humanized to reduce immunogenicity to humans, while having at least the same affinity (or superior affinity) of the parental non-human antibody. In preferred embodiments, the antibodies of the present disclosure are humanized antibodies of the parent antibody A24. Generally, a humanized antibody comprises one or more variable domains in which, CDRs, (or portions thereof) are derived from a non-human antibody, e.g. the murine A24 antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g. the A24 antibody from which the CDR residues are derived), e.g., to restore or improve antibody specificity or affinity. In some specific embodiments, some CDR residues in a humanized antibody are also substituted, e.g. to restore or improve antibody specificity or affinity. Humanized antibodies and methods of making them are reviewed, e.g. in Almagro and Fransson, Front. Biosci. 13: 1619-1633 (2008), and are further described, e.g., in Riechmann et al., Nature 332:323-329 (1988); Queen et al., Proc. Natl Acad. Sci. USA 86: 10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling). Preferably the recombinant antibody according to the disclosure is a humanized silent antibody, preferably a humanized silent IgG1 or IgG4 antibody.

As used herein, the term "silent" antibody refers to an antibody that exhibits no or low ADCC activity as measured in an ADCC activity assay.

In one embodiment, the term "no or low ADCC activity" means that the silent antibody exhibit an ADCC activity that is at least below 10%, for example below 50% of the ADCC activity that is observed with the corresponding antibody with wild type human IgG1 isotype.

Silenced effector functions can be obtained by mutation in the Fc constant part of the antibodies and have been described in the Art: Strohl 2009 (AA & N297A); Baudino 2008, D265A (Baudino et al., J. Immunol. 181 (2008): 6664-69, Strohl, CO Biotechnology 20 (2009): 685-91). Examples of silent IgG1 antibodies comprise the so-called AA mutant comprising L234A and L235A mutation in the IgG1 Fc amino acid sequence. Another silent IgG1 antibody comprises the N297A mutation, which results in aglycosylated or non-glycosylated antibodies.

Antibodies with mutant amino acid sequences can be obtained by mutagenesis (e.g. site-directed or PCR-mediated mutagenesis) of the coding nucleic acid molecules, followed by testing of the encoded altered antibody for retained function (i.e. the functions set forth above) using the functional assays described herein.

Antibodies with Conservative Modifications

In certain embodiments, an antibody (or a binding protein comprising antigen binding portion thereof) of the disclosure has a heavy chain variable region comprising HCDR1, HCDR2, and HCDR3 sequences and a light chain variable region comprising LCDR1, LCDR2, and LCDR3 sequences, wherein one or more of these CDR sequences have specified amino acid sequences based on the mAb1 to mAb16 antibodies described herein or conservative modifications thereof, and wherein the antibody or protein retains the desired functional properties of the anti-TfR antibodies of the disclosure.

Desired functional properties of the anti-TfR antibodies includes without limitation:

(i) it binds to the transferrin receptor with a KD of 10 nM or less, preferably with a $K_D$ of 1 nM or less, for example as measured by SPR assay, for example using Biacore®;

(ii) it binds to the transferrin receptor with an $EC_{50}$ of 0.1 μg/ml or below, preferably of 0.05 μg/ml or below, as measured in an ELISA assay (see PCT/EP2016/067465 for more information);

(iii) it induces apoptosis of HL-60 cell line to a level equal or superior to the induction level measured with the corresponding reference chimeric antibody having the parental murine variable regions with VH of SEQ ID NO:9 and VL of SEQ ID NO:10, for example as measured using the HL-60 apoptosis induction assay.

Typically, an amount of 10 μg/ml of a recombinant antibody of the present disclosure may be assayed for induction of apoptosis of HL-60 cell line as compared to the same amount of the reference chimeric antibody with the parental murine variable regions of A24 comprising VH of SEQ ID NO:9 and VL of SEQ ID NO:10. Induction of apoptosis in the HL-60 apoptosis induction assay of a tested antibody is equal to a reference antibody if the percentage of positive cells as measured with the tested antibody is not significantly lower that the percentage of positive cells as measured with the reference antibody.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Modifications can be introduced into an antibody of the disclosure by standard techniques known in the art, such as site-directed mutagenesis and PCR-mediated mutagenesis.

Framework or Fc Engineering

Engineered antibodies of the disclosure include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody.

In particular, the company Antitope (Cambridge UK) has developed a range of proprietary technologies for assessing and removing immunogenicity, which are based on identifying the location of T cell epitopes in therapeutic antibodies and proteins. These technologies are summarized below:

iTope™—an in silico technology for prediction of peptide binding to human MHC class II alleles (Perry et al. 2008 *Drugs in R&D,* 9(6):385-396).

TCED™—a database of known T cell epitopes identified in studies using EpiScreen™ T cell epitope mapping assays especially of antibody V regions (Bryson et al. 2010 *Biodrugs* 24(1):1-8). The database can be interrogated by BLAST searching to identify common motifs (Altschul et al. 1997 *Nucleic Acids Res.* (1997) 25:3389-3402).

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity.

Furthermore, an antibody of the disclosure may be chemically modified (e.g. one or more chemical moieties can be attached to the antibody) or be modified to alter its glycosylation, again to alter one or more functional properties of the antibody. Each of these embodiments is described in further detail below.

As used herein, the term "isotype constant region" or "Fc region" is used interchangeably to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the disclosure may comprise antibody populations with all K447 residues removed, antibody populations with no K447 residues removed, and antibody populations having a mixture of antibodies with and without the K447 residue.

In one specific embodiment, the hinge region of CH1 is modified such that the number of cysteine residues in the hinge region is altered, e.g. increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR, FcγRII, FcγRIII and FcRn have been mapped and variants with improved binding have been described (see Shields, R. L. et al., 2001 J. Biol. Chem 276:6591-6604).

In other embodiments, the Fc region is modified to decrease the ability of the antibody to mediate antibody dependent cellular cytotoxicity (ADCC) and/or to decrease the affinity of the antibody for an Fcγ receptor by modifying one or more amino acids. Such antibodies with decreased effector functions, and in particular decreased ADCC include silent antibodies.

In certain embodiments, the Fc domain of the IgG1 isotype is used. In some specific embodiments, a mutant variant of the IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant is IgG1 wherein Leucine is replaced by Alanine at amino acid positions 234 and 235 as described in J. Virol 2001 December; 75(24):12161-8 by Hezareh et al.

In certain embodiments, the Fc domain is a silent Fc mutant preventing glycosylation at position 297 of the Fc domain. For example, the Fc domain contains an amino acid substitution of asparagine at position 297. An example of such amino acid substitution is the replacement of N297 by a glycine or an alanine.

In still another embodiment, the glycosylation of an antibody is modified. For example, an aglycoslated antibody can be made (i.e. the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1 176 195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the disclosure are produced by recombinant expression in a cell line which exhibits a hypofucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g. beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 *Nat. Biotech.* 17:176-180).

Another modification of the antibodies herein that is contemplated by the present disclosure is pegylation or hesylation or related technologies. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another modification of the antibodies that is contemplated by the present disclosure is a conjugate or a protein fusion of at least the antigen-binding region of the antibody of the disclosure to serum protein, such as human serum albumin or a fragment thereof to increase half-life of the resulting molecule. Such approach is for example described in Ballance et al. EP 0 322 094.

Another possibility is a fusion of at least the antigen-binding region of the antibody of the disclosure to proteins capable of binding to serum proteins, such human serum albumin to increase half-life of the resulting molecule. Such approach is for example described in Nygren et al., EP 0 486 525.

In one specific embodiment, the effector function or complement activation function of an antibody according to the disclosure has been reduced or eliminated relative to a wild-type antibody of the same isotype. In one aspect, the effector function is reduced or eliminated by a method selected from reduction of glycosylation of the antibody, modification of the antibody isotype to an isotype that naturally has reduced or eliminated effector function, and modification of the Fc region. In specific related embodiment, said isotype with reduced or eliminated effector function is IgG4 isotype.

Production of Antibodies of the Disclosure

Antibodies of the disclosure can be obtained using conventional technical known to those of skill in the art. For more information about nucleic acids encoding antibodies of the disclosure as well as generation of transfectomas producing these antibodies, those of skill in the art can also refer to international application number PCT/EP2016/067465.

Linkers

ADC of the disclosure contains three different linkers: L, Z and X. General formula of these three linkers linked together is represented by formula (V). Linkers allow linkage between the antibody and the drug. Preferably, linkage is covalent. Therefore, in an embodiment of the invention, D is covalently bonded to X and/or X is covalently bonded to Z and/or Z is covalently bonded to L and/or L is covalently bonded to Ab. More preferably, D is covalently bonded to X and X is covalently bonded to Z and Z is covalently bonded to L and L is covalently bonded to Ab.

L is a linker molecule of formula (II) or (IV), wherein n is an integer comprised between 2 and 20. L is a PEG-arylpropiolonitril, also called "APN". As disclosed herein, n encompasses then 2, 3, 4, 5, 6, 7, 8, 9, 10, 11, 12, 13, 14, 15, 16, 17, 18, 19 and 20. L confers stability of ADC in a wide range of conditions. More information about L is disclosed in PCT/EP2014/064387.

In an embodiment, which can be combined with other embodiments, L is linked to antibody via at least one thiol moiety (from an antibody's cystein). In an embodiment, linkage between L and the antibody is on the side of the double bond $C{=}C$ in formula (II) or (IV).

Z is a dipeptide of valine-citrulline bonded to L. Z is linked to L on the side of carbonyl group (i.e. carbonyl function) in L. In an embodiment, linkage between L and Z occurs between the carbonyl group of L and the amino function of Z (e.g. amino function of valine). Dipeptide VC is a cleavable linker. Cleavable linkers exploit the differences between conditions in the blood stream and the cytoplasmic conditions within target cells (notably cancer cells). Dipeptide VC is cleaved in the acidic environment within lysosomes by lysosomal proteases, such as cathepsin B. After internalization of ADC in target cells, there is an intracellular cleavage mechanism by cathepsin B, between Z and X (e.g. cleavage between the citrulline and aminobenzyl ester self-immolative group on the side of the amine function (see ➡ in formula (VII):

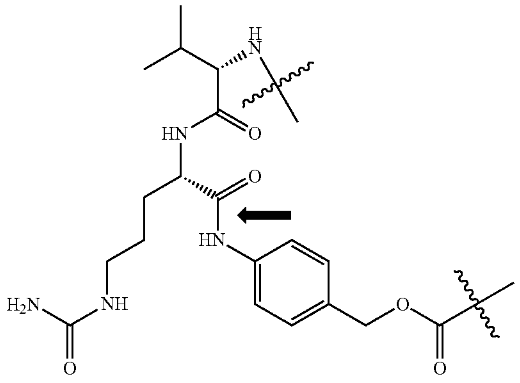 [SMILES: *N[C@H](C(=O)N[C@@H](CCCNC(N)=O)C(=O)Nc1ccc(COC(*)=O)cc1)C(C)C]

The resultant X-drug is not a stable intermediate and spontaneously undergoes elimination leaving drug as the product (i.e. a 1,6-elimination (self-immolation)). For more information about valine-citrulline dipeptide as an intracellular cleavage mechanism by cathepsin B, see for example Dubowchik G M, Firestone R A, Padilla L, Willner D, Hofstead S J, Mosure K, et al. Bioconjug Chem. 2002; 13:855-69.

X is an aminobenzyl ester self-immolative group bonded to Z of formula (III). X is linked to Z on the side of the carboxylic group (i.e. carbonyl function) of Z. In an embodiment, linkage between Z and X occurs between the carbonyl group of Z and the amino function of X. For more information about aminobenzyl ester self-immolative group, see WO 03/026577 or WO 2004/010957. As disclosed herein, X is therefore a bifunctional chemical moiety spacer, which (i) is capable of covalently linking together at least two other chemical moieties into a stable molecule (notably D and Z), (ii) can be released from one of the spaced chemical moieties from the molecule by means of enzymatic cleavage (after cleavage by cathepsin B, X-D is released); and (iii) following enzymatic cleavage, can spontaneously cleave from the remainder of the molecule to release the other of the spaced chemical moieties (finally D is released).

Payloads

In one embodiment, D of the disclosure is a payload which is linked to X on the side of the carbonyl function of X. In an embodiment, linkage between X and D occurs between carbonyl function of X and amino group of D.

In a specific embodiment, in ADC of the disclosure, D is a cytotoxic drug.

In an embodiment, the cytotoxic drug is selected from the group consisting of: taxon, cytochalasin B, auristatin, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. This includes also antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Preferably, the drug is monomethyl auristatin E.

ADC of the Disclosure

In an embodiment, the present disclosure provides ADC where an anti-TfR antibody is linked to a drug (notably MMAE). Linkers are molecules L, Z and X as defined above. Preferably such ADC can selectively deliver an effective dose of a MMAE to tumor tissues expressing TfR.

In an embodiment, the present disclosure provides ADC of formula (I) as defined above.

In a more preferred embodiment, ADC of the disclosure is as follows:

- Ab is an anti-TfR antibody, notably mAb1 as defined above,
- L is a linker molecule bonded to said antibody, said linker molecule being of formula (IV),
- Z is a dipeptide of valine-citrulline bonded to L,
- X is bonded to Z and is a para-aminobenzyl ester self-immolative group of formula (III) wherein m is 0,
- D is a drug bonded to X, notably MMAE.

In another more preferred embodiment, ADC of the disclosure called "INA01-SDV1" is as follows:

- Ab is the anti-TfR antibody mAb1 characterized by a Heavy Chain represented by SEQ ID NO:18 and a Light Chain represented by SEQ ID NO:17,
- L is a linker molecule bonded to said antibody, said linker molecule being of formula (IV),
- Z is a dipeptide of valine-citrulline bonded to L,
- X is bonded to Z and is a para-aminobenzyl ester self-immolative group of formula (III) wherein m is 0,
- D is MMAE.

Figure 1:
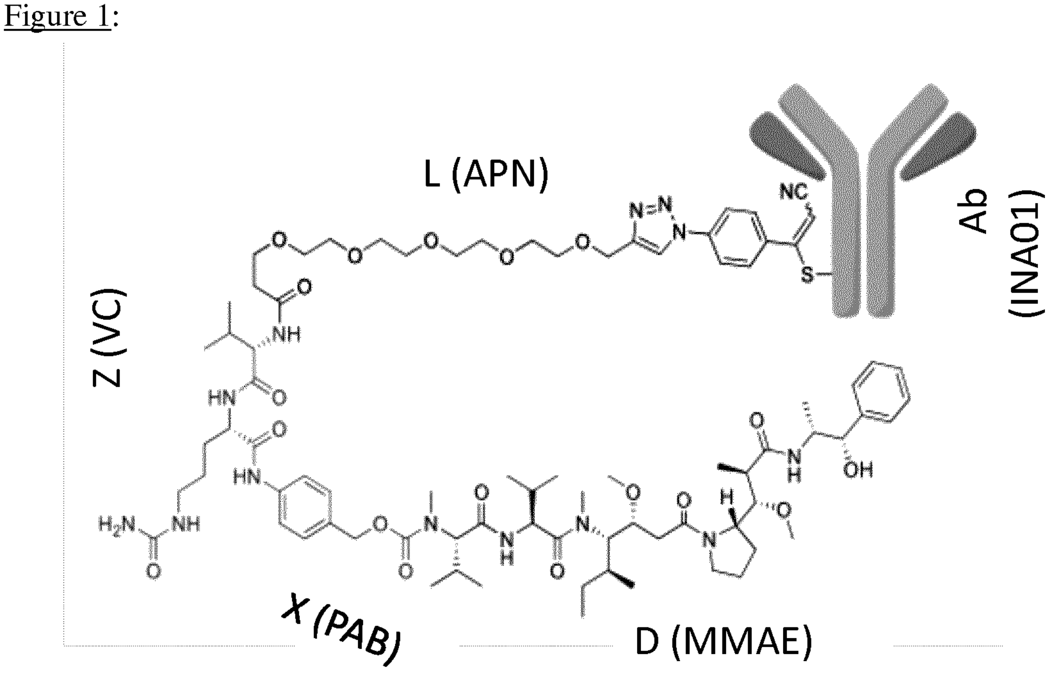
FIG. 1 represents a schematic representation of ADC called “INA01-SDV1” or “INA01-SDV #1”. INA01 corresponds to Ab, APN corresponds to L, VC-PAB corresponds to Z—X respectively and MMAE corresponds to D.

FIG. 1 represents a schematic representation of one of the preferred ADC of the disclosure, named "INA01-SDV1" or "INA01-SDV #1". To the humanized antibody INA01 (Ab) has been attached through the cysteine residues the linker APN (L), a dipeptide sequence valine-citrulline cleavable by the enzyme Cathepsin B (Z), a para-aminobenzyl ester of formula (III) wherein m is 0 (X), and the cytotoxic monomethyl auristatin E 'MMAE' (D).

While the drug to antibody ratio has an exact value for a specific ADC it is understood that the value will often be an average value when used to describe a sample containing many ADC, due to some degree of inhomogeneity, typically associated with the conjugation step. The average loading for a sample of an ADC is referred to herein as the drug to antibody ratio, or "DAR." In some embodiments, the DAR is between about 1 and about 8 (i.e. 1, 1.5, 2, 2.5, 3, 3.5, 4, 4.5, 5, 5.5, 6, 6.5, 7, 7.5 and 8), preferably at the average around 4.

Pharmaceutical Compositions—Formulations

In another aspect, the present disclosure provides a composition, e.g. a pharmaceutical composition, containing one or a combination of ADC disclosed herein, (for example, one ADC selected from the group consisting of mAb1-mAb16, notably mAb1, bounded to a linker molecule of formula (IV), itself bounded to Z, itself bounded to X which is a para-aminobenzyl ester self-immolative group of formula (III) wherein m is 0, itself bounded to a drug such as MMAE), formulated together with a pharmaceutically acceptable carrier.

In a preferred embodiment, the composition of the disclosure (e.g. a formulation) contains (i) one or a combination of ADC disclosed herein, (for example, one ADC selected from the group consisting of mAb1-mAb16, notably mAb1, bounded to a linker molecule of formula (IV), itself bounded to Z, itself bounded to X which is a para-aminobenzyl ester self-immolative group of formula (III) wherein m is 0, itself bounded to a drug such as MMAE), (ii) histidine, (iii) and optionally a pharmaceutically acceptable carrier, and the pH of said composition is 6.5. In another embodiment, the composition of the disclosure (e.g. a formulation) contains (i) one or a combination of ADC disclosed herein, (ii) histidine (iii) sucrose, (iv) polysorbate 80, and the pH of said composition is 6.5. Preferably, the molar concentration of histidine is 20 mM. In another embodiment, the composition of the disclosure (e.g. a formulation) contains (i) one or a combination of ADC disclosed herein, (ii) 20 mM histidine, (iii) 6% sucrose (6 g for 100 mL of buffer), (iv) 0.02% polysorbate 80, and the pH of said composition is 6.5. Preferably, such compositions are stable at 40° C., meaning the average DAR of the ADC is maintained between 4 and 4.5. pH can be determined by any techniques known by those skilled in the art.

Pharmaceutical compositions disclosed herein also can be administered in combination therapy, i.e. combined with other agents. For example, the combination therapy can include ADC of the present disclosure, combined with at least one anti-viral, anti-inflammatory or another anti-proliferative agent. Examples of therapeutic agents that can be used in combination therapy are described in greater detail below in the section on uses of the ADC of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion). In one embodiment, the carrier should be suitable for subcutaneous route. Depending on the route of administration, the active compound, i.e. ADC, may be coated in a material to protect the compound from the action of acids and other natural conditions that may inactivate the compound. Sterile phosphate-buffered saline is one example of a pharmaceutically acceptable carrier. Other suitable carriers are well-known to those in the art. (See e.g. Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, . . . .

The form of the pharmaceutical compositions, the route of administration, the dosage and the regimen naturally depend upon the condition to be treated, the severity of the illness, the age, weight, and sex of the patient, . . . .

The pharmaceutical compositions of the disclosure can be formulated for a topical, oral, parenteral, intraperitoneal, intranasal, intravenous, intramuscular, subcutaneous or intraocular administration and the like, preferably intraperitoneal or intravenous.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the ADC may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilisates for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An ADC of the disclosure can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The ADC of the disclosure may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles can be contemplated. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present disclosure, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Uses and Methods of the ADC of the Disclosure

ADC of the present disclosure have in vitro and in vivo diagnostic and therapeutic utilities. For example, these molecules can be administered to cells in culture, e.g. in vitro or in vivo, or in a subject, e.g. in vivo, to treat, prevent or diagnose a variety of disorders.

ADC of the disclosure can not only inhibit cell proliferation, but also induce apoptosis of highly proliferating cells, such as activated T cells.

It is the contemplated herein to use the ADC of the present disclosure as a medicament, in particular for use in treating, preventing or diagnosing cell proliferative disorders, such as tumors expressing a high level of TfR, more specifically, hematologic tumors, such as lymphoma, and in particular, ATL, MCL, Hodgkin Disease, Large B cell lymphoma, Peripheral T cell lymphoma, Acute leukaemia (Myeloid and Lymphoid) as well as solid tumors, such as Renal Carcinoma, Lung cancer (small cells), Breast cancer . . . .

It is further disclosed ADC of the present disclosure for use in treatment of a solid tumor.

The ADC for use as disclosed above may be administered as the sole active ingredients or in conjunction with, e.g. as an adjuvant to or in combination to, other drugs e.g. anti-viral, anti-inflammatory agents or cytotoxic, anti-proliferative, chemotherapy or anti-tumor agents, e.g. for the treatment or prevention of diseases mentioned above. For example, the ADC for use as disclosed above may be used in combination with AZT, IFN-alpha, anti-CD20 mAb, anti-CD25 mAb, anti-PD1 mAb, anti-PDL-1 mAb, chemotherapy agents. Suitable antineoplastic agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as Paclitaxel, Docetaxel), epothilones, inhibitors of Topoisomerase I (such as Irinotecan or Topotecan), inhibitors of Topoisomerase II (such as Etoposide, teniposide, or Tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as carboplatin, cisplatin and oxaliplatin), retinoids (such as tretinoin, alitretinoin, bexarotene), vinca alkaloids and derivatives (such as vinblastine, vincristine, vindesine, vinorelbine), targeted therapies such as kinase inhibitors (such as Ibrutinib, Idelalisib, Erlotinib, Gefitinib, Imatinib, Vemurafenib, Vismodegib), proteasome inhibitors (such as bortezomib, carfilzomib), histone deacetylase inhibitors (such as Vorinostat or Romidepsin).

In accordance with the foregoing the present disclosure provides in a yet further aspect a method comprising administration of a therapeutically effective amount of an ADC of the disclosure.

In accordance with the foregoing the present disclosure provides in a yet further aspect a method comprising co-administration, e.g. concomitantly or in sequence, of a therapeutically effective amount of an ADC of the disclosure, and at least one second drug substance, said second drug substance being an anti-viral or anti-proliferative agent, e.g. as indicated above.

Also within the scope of the present disclosure are kits consisting of the compositions (e.g. comprising ADC) disclosed herein and instructions for use. The kit can further contain a least one additional reagent, or one or more additional antibodies or proteins (e.g. an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an ADC treatment, as defined above.

Process of Making ADC of the Disclosure

Antibodies of the disclosure can be conjugated to at least one drug by linkers L-Z—X by any techniques known in the art. Such techniques are for example described in U.S. Pat. Nos. 7,811,572; 7,368,565; US 2011/0003969; US 2011/0166319; US 2012/0253021 and US 2012/0259100. For more information relative to methods for conjugating therapeutic agents to antibodies, see also Panowksi S et al. 2014 Jan. 1; 6(1): 34-45 for a review on antibody drug conjugates.

In an embodiment, a process for obtaining ADC of the disclosure comprises the following steps:

culturing a host cell under conditions suitable for expression of a nucleic acid encoding the antibody as defined above, isolating the antibody, synthesis of the monomethyl auristatin E bonded to the linker L-Z—X of formula (V), conjugating said antibody to monomethyl auristatin E bonded to the linker L-Z—X of formula (V).

Antibodies can be obtained as explained above. Antibodies contain four interchain disulfide bonds that can be used as potential conjugation sites. The four interchain disulfide bonds can be reduced, for example by tris(2-carboxyethyl) phosphine (TCEP) or dithiothreitol (DTT), which results in eight thiol groups that are available for conjugation.

Linker L can be obtained as disclosed in PCT/EP2014/064387. Linker X can be obtained as disclosed in WO 03/026577 or WO 2004/010957. Linker Z is also well known by those skilled in the art who know how to obtain it.

The invention having been fully described is now further illustrated by the following examples, which are illustrative only and are not meant to be further limiting.

EXAMPLES

Example 1: Comparison of Binding Between A24 and INA01-SDV1 on Hematopoietic Cell Lines Serial dilutions (5 to 0.05 ug/mL) of both biotinylated antibodies (antibody A24 and antibody of ADC INA01-SDV1) were performed and incubated on THP-1 and MEC-1 cell lines. The binding of the diluted antibodies was detected by Flow cytometry using streptavidin Alexa F488 (available at ThermoFisher scientific).

Figure 2A:
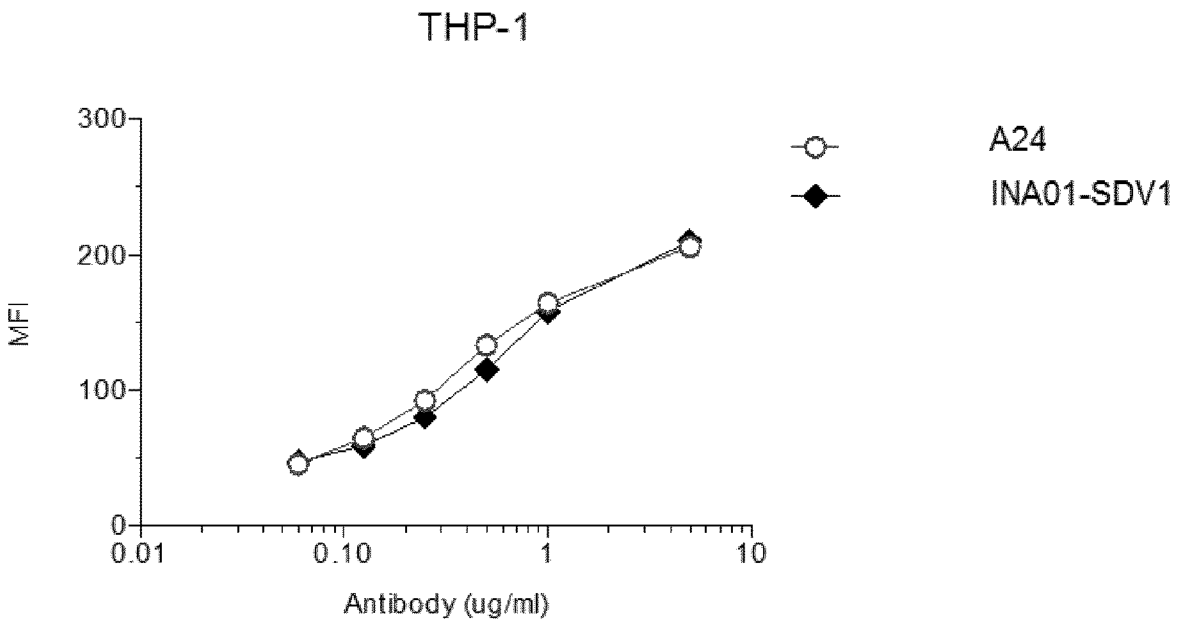
FIG. 2A represents results with THP-1 cell line and FIG. 2B represents results with MEC-1 cell line.
Figure 2B:
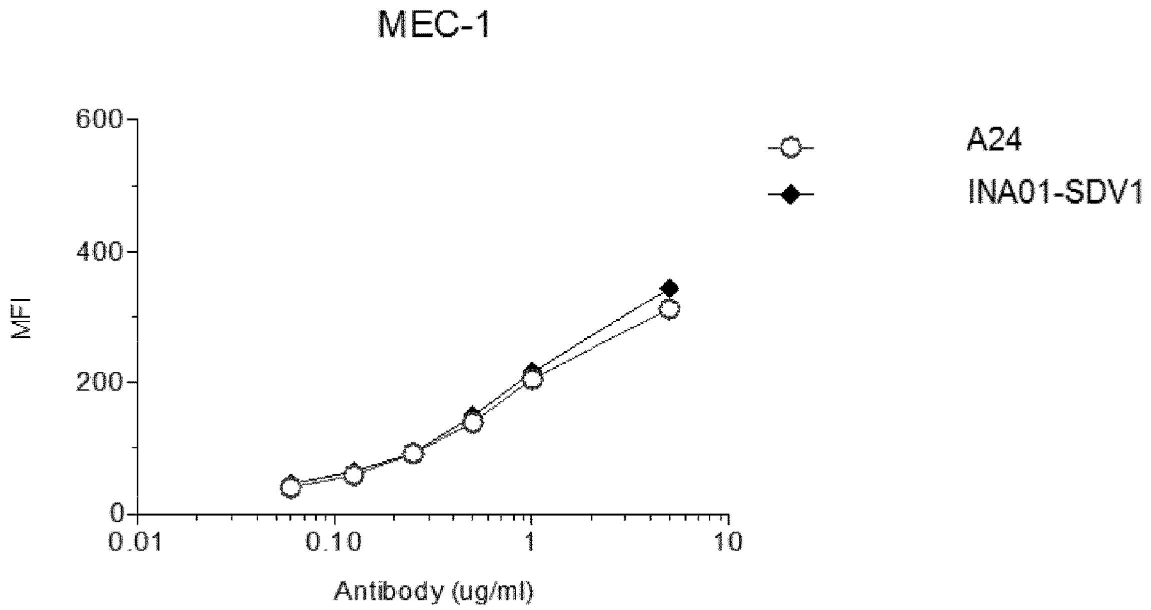

Both A24 and INA01-SDV1 show identical affinity to the $CD71^+$ cell lines (FIGS. 2A and 2B).

Example 2: Apoptosis

CHO cells were transfected with human CD71 and clones were selected by FACS. Native CHO cells (negative for human CD71) and hCD71 positive cells were incubated with several concentrations of INA01-SDV #1 for 96 hours in complete media a 37° C. At day 4, cells were incubated with Annexin V and Topro 3. Apoptotic cells were determined by FACS as double positive Annexin V/Topro 3 cells.

Figure 3A:
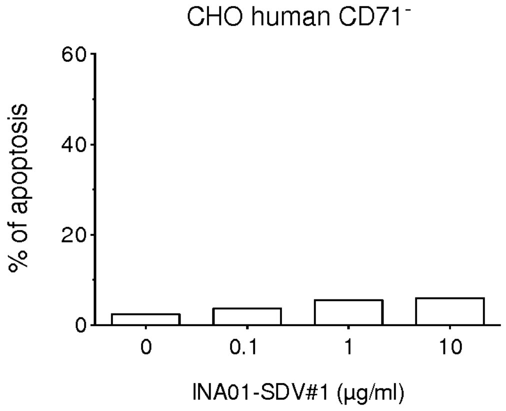
FIG. 3A represents results with CD71 negative cells and FIG. 3B represents results with CD71 positive cells.
Figure 3B:
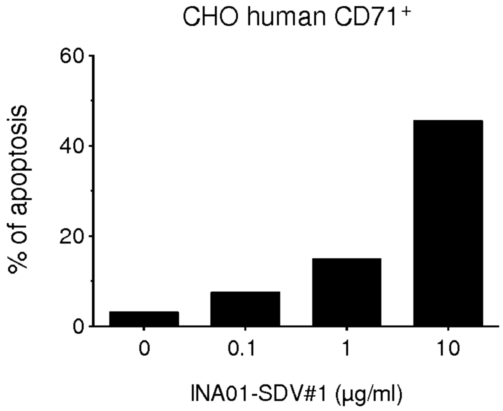

Results are presented on FIGS. 3A and 3B. Bars represent the percentage of apoptotic cells.

Example 3: In Vitro Efficacy of INA01-SDV #1 on Multiple Cell-Lines

Inhibition of cell proliferation was measured by using the cell viability assay CellTiter-Glo® by Promega according the manufacturer protocol. Briefly, cells were plated in 48-wells plate and incubated during 96 hours in presence or not of increasing concentration of INA01-SDV1 (from 0 to 20 g/ml).

Figure 4A:
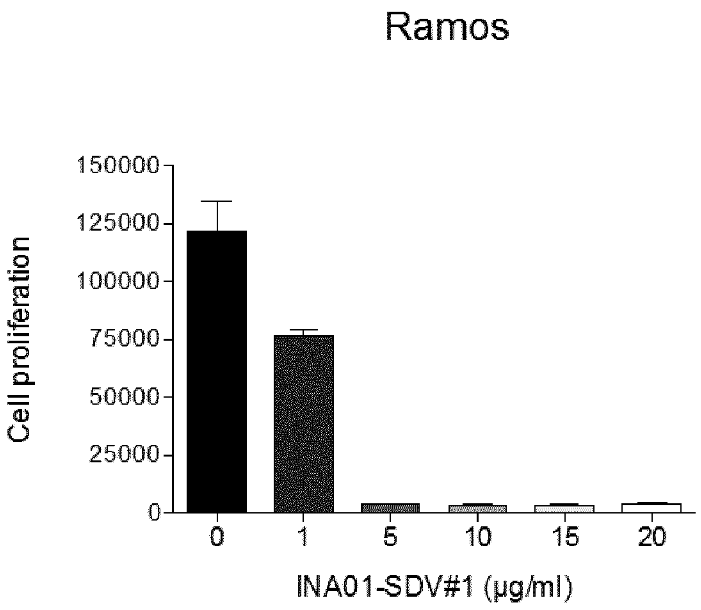
FIG. 4A represents results with Ramos cell line and FIG. 4B represents results with THP-1 cell line.
Figure 4B:
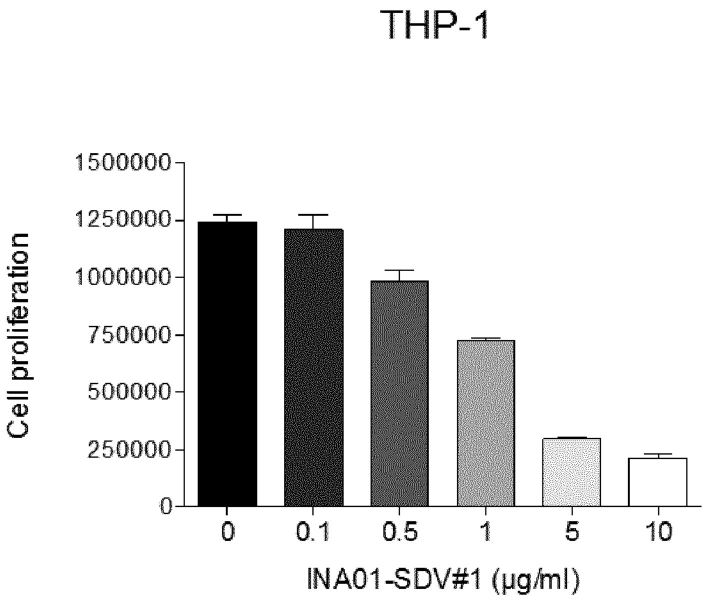

Results are presented on FIGS. 4A and 4B. Cellular viability was impaired in both Ramos and THP-1 cell lines.

Example 4: In Vivo Efficacy of INA01-SDV1

To assess the in vivo efficacy of the INA01-SDV #1, nude mice were injected subcutaneously with $5\times10^6$ THP-1 cells. When tumors reach 100 $mm^3$, mice were injected in a curative mode with either 5 mg/kg, 0.5 mg/kg or PBS intra-peritoneal. Tumor growths were monitored every day and mice were sacrificed when the tumors reach 1000 $mm^3$.

The data of FIG. 5 represent the survival of the mice in days after the single injection of INA01-SDV #1.

Example 5: Toxicologic Analysis

Toxicology analysis of the INA01-SDV #1 was assessed in wild-type B6 (WT) mice and CD71/transferrin double knocking mice (TfR/Tf 2Ki). Mice were injected IP with 5 injections of INA01-SDV #1 at 3 mg/kg every 4 days and sacrificed two days after the last injection.

FIG. 6 represents the macroscopic organ analysis in WT (FIG. 6A) and TfR/Tf 2Ki mice (FIG. 6B). Table 7 below represents the independent pathological analysis of each organ depicted in FIGS. 6A and 6B.

TABLE 7

Independent pathological analysis of each organ depicted in FIGS. 6A and 6B

| Genotype | Wild-type mouse | TfR/Tf KI mouse |
|---|---|---|
| Treatment | 5 injections at 3 mg/kg every 4 days | 5 injections at 3 mg/kg every 4 days |
| Kidney | N/A | N/A |
| Heart | Irregularity in some disperse nucleus. Some Irregularities in cell density | Irregularity in some disperse nucleus. Some Irregularities in cell density |
| Spleen | Small hematopoiesis in the red pulp | Small hematopoiesis in the red pulp |
| Lung | Some macrophages | Some macrophages |
| Liver | Small hematopoiesis No necrosis No Steatosis No Fibrosis | Small hematopoiesis No necrosis No Steatosis No Fibrosis |
| Brain | N/A | N/A |

Example 6: Formulations 4 different formulations have been compared. Formulations 1 and 2 only differ by their pH, as well as formulations 3 and 4. Formulations contain ADC, 20 mM histidine or 20 mM citrate, 6% sucrose (6 g for 100 mL of buffer) and 0.02% polysorbate 80.

Formulation 1 contains an ADC according to the disclosure, notably INA01, and histidine, pH of this formulation is 5.5. Formulation 2 contains an ADC according to the disclosure, notably INA01, and histidine, pH of this formulation is 6.5. Formulation 3 contains an ADC according to the disclosure, notably INA01, and citrate, pH of this formulation is 5.5. Formulation 4 contains an ADC according to the disclosure, notably INA01, and citrate, pH of this formulation is 6.5.

Results are depicted in Table 8 below. They indicate DAR (drug antibody ratio) values for formulations 1 to 4 at T=0 and T=2 weeks storage at 5° C./40° C. and T=4 weeks storage at 5° C./25° C. At 40° C., an overall decrease of DAR values is measured, except with formulation 2. These results show that formulation 2 is stable, by comparison with formulations 1, 3 and 4.

TABLE 8

Comparison of 4 formulations

| Sample | T = 0 | T = 2 Weeks | T = 4 Weeks |
|---|---|---|---|
| Formulation 1 (Histidine, pH5.5) | 4.2 | 4.1 (5° C.) 3.6 (40° C.) | 4.3 (5° C.) 4.3 (25° C.) |
| Formulation 2 (Histidine, pH6.5) | 4.2 | 4.1 (5° C.) 4.0 (40° C.) | 4.3 (5° C.) 4.3 (25° C.) |
| Formulation 3 (Citrate, pH5.5) | 4.2 | 4.1 (5° C.) 2.1 (40° C.) | 4.2 (5° C.) 4.2 (25° C.) |
| Formulation 4 (Citrate, pH6.5) | 4.1 | 4.1 (5° C.) 3.8 (40° C.) | 4.3 (5° C.) 4.3 (25° C.) |

Example 7: Determination of the $IC_{50}$

HL-60 acute myeloid leukemia cell line (i.e. cells expressing CD71) was incubated at 37° C. with 10 concentrations of INA01-SDV #1 ranging from 0.02 to 10 ug/mL. The effect of ADC on cell proliferation is shown in FIG. 7. The fitted curve was used to calculate the $IC_{50}$. Therefore, the calculated $IC_{50}$ of INA01-SDV #1 is 0.08 ug/mL.

Example 8: Secretion of TNF-α

To assess if INA01-SDV #1 could induce a cytokine release syndrome (CRS) in patients, TNF-α secretion by peripheral blood mononuclear cells (PBMC) was tested. TNF-α production was tested after incubation of PBMC with INA01-SDV #1 in three different conditions which represent different concentration of the ADC: highly coated (air-dried), lower coated (wet-coated) or in solution (aqueous).

Material and Methods

PBMC were separated by Ficoll and suspended in culture medium with INA01-SDV #1 Air-dried, wet-coated or aqueous at 0.1, 1 or 10 μg/ml as previously reported for several activation procedures (Findlay L et al. J. Immunol. Meth 2008; Stebbings R et al. J. Immunol. 2007). After incubation for 24 hours at 37° C., TNF-α was assessed by enzyme-linked immunosorbent assay (ELISA). A DuoSet ELISA Development kit that contains the basic components required for the development of sandwich ELISAs to measure natural and recombinant human TNF-alpha were used.

INA01-SDV #1 Coating

INA01-SDV #1 is presented to PBMC in three different protocols: Air-dried, wet-coated or aqueous.

- Air-dried: INA01-SDV #1 was added at 5× working concentration in 50 ul (for a final concentration of 0.1, 1 and 10 μg/ml). The plate was kept under the hood overnight, then washed twice.
- Wet-coated: INA01-SDV #1 was added at 5× working concentration in 200 ul (for a final concentration of 0.1, 1 and 10 μg/ml). The wells were taped to avoid drying, then washed twice.
- Aqueous: PBMC and INA01-SDV #1 were cultured together in the culture medium.

Results

The results are on FIG. 8 and show that no TNF-α was released in all INA01-SDV #1 incubation conditions on PBMC. However, 24 hour incubation with 1 ng/ml of LPS produced a strong release of TNF-α.

Example 9: In Vivo Efficacy of INA01-SDV #1 after IP Administration

To assess the in vivo efficacy of the INA01-SDV #1, nude mice were injected subcutaneously with $5\times10^6$ THP-1 cells. When tumors reach 100 $mm^3$, mice were injected in a curative mode, every 4 days for 4 doses, with either 1 mg/kg, 0.5 mg/kg or PBS intra-peritoneal. Tumor growths were monitored every day and mice were sacrificed when the tumors reach 1000 $mm^3$.

The data of FIG. 9 represent the survival of the mice in days after the four injections intraperitoneally of INA01-SDV #1.

Example 10: In Vivo Efficacy of INA01-SDV #1 after IV Administration

To assess the in vivo efficacy of the INA01-SDV #1, nude mice were injected subcutaneously with $5\times10^6$ THP-1 cells. When tumors reach 100 $mm^3$, mice were injected in a curative mode, every 4 days for 4 doses, with either 3 mg/kg, 0.5 mg/kg or PBS intravenous. Tumor growths were monitored every day and mice were sacrificed when the tumors reach 1000 $mm^3$.

The data of FIG. 10 represent the survival of the mice in days after the four injections intravenously of INA01-SDV #1.

The invention claimed is:

1. An antibody-drug conjugate of the formula (I): Ab-L-Z—X-D, wherein:

Ab is an anti-TfR antibody chosen among a full-length antibody or a bivalent fragment, which comprises:

(a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6, (b) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:8 and LCDR3 of SEQ ID NO:6, (c) a variable heavy chain polypeptide comprising VH of SEQ ID NO:11 and a variable light chain polypeptide comprising VL of SEQ ID NO:13, (d) a variable heavy chain polypeptide comprising VH of SEQ ID NO:11 and a variable light chain polypeptide comprising VL of SEQ ID NO:14, (e) a variable heavy chain polypeptide comprising VH of SEQ ID NO:12 and a variable light chain polypeptide comprising VL of SEQ ID NO:13, or (f) a variable heavy chain polypeptide comprising VH of SEQ ID NO:12 and a variable light chain polypeptide comprising VL of SEQ ID NO:14, L is a linker molecule bonded to said anti-TfR antibody, said linker molecule being of formula (II):

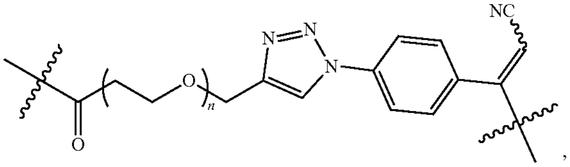
, wherein n is an integer comprised from 2 and 20 inclusive,

Z is a dipeptide of valine-citrulline bonded to L,

X is an aminobenzyl ester self-immolative group bonded to Z,

D is a drug monomethyl auristatin E bonded to X.

2. The antibody-drug conjugate according to claim 1, wherein X is a para-aminobenzyl ester group covalently bonded to Z, said X being of the following formula (III):

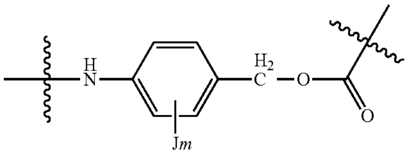
,

J being an optional substituent chosen among F, Cl, Br, $NO_2$, $NHCOCH_3$, $N(CH_3)_2$, $NHCOCF_3$, alkyl, and haloalkyl, and m being an integer of 0, 1, 2, 3 and 4.

3. The antibody-drug conjugate according to claim 1, wherein Lis covalently bonded to one or more thiol residues of said antibody.

4. The antibody-drug conjugate according to claim 1, wherein said anti-TfR antibody specifically binds to the transferrin receptor of SEQ ID NO:16.

5. The antibody-drug conjugate according to claim 1, wherein said anti-TfR antibody binds to the transferrin receptor with a KD of 10 nM or less, preferably with a KD of 1 nM or less.

6. The antibody-drug conjugate according to claim 1, wherein said anti-TfR antibody is a monoclonal antibody and/or a humanized antibody.

7. The antibody-drug conjugate according to claim 1, wherein:

said anti-TfR antibody comprises a human IgG4 isotype constant region, or a mutant or chemically modified constant region, wherein said mutant or chemically modified constant region confers no or decreased ADCC activity to said anti-TfR antibody when compared to a corresponding antibody with wild type IgG1 isotype constant region, or said anti-TfR antibody comprises a human IgG1 isotype constant region, or a mutant or chemically modified constant region, wherein said mutant or chemically modified constant region confers increased ADCC activity to said anti-TfR antibody when compared to a corresponding antibody with wild type IgG1 isotype constant region.

8. A method of treating a tumor in a subject in need thereof, comprising administering to the subject a therapeutically effective amount of the antibody-drug conjugate according to claim 1, wherein the therapeutically effective amount is sufficient to treat the tumor.

9. A pharmaceutical composition comprising an antibody-drug conjugate according to claim 1, in combination with one or more pharmaceutically acceptable excipients, diluents or carriers.

10. A composition comprising an antibody-drug conjugate according to claim 1, said composition having a pH of 6.5 and further comprising histidine, and optionally sucrose and polysorbate 80.

11. A lyophilisate formulation, a pre-filled syringe or a vial comprising an antibody-drug conjugate according to claim 1.

12. A process for obtaining an antibody-drug conjugate according to claim 1, wherein the method comprises:

culturing a host cell under conditions suitable for expression of a nucleic acid encoding the antibody as defined in claim 1, isolating the antibody, synthesizing monomethyl auristatin E bonded to the linker L-Z—X of formula (V):

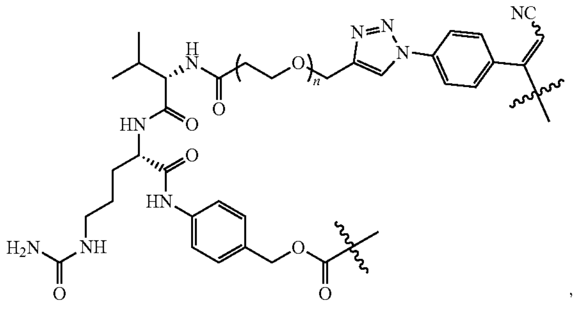

conjugating said antibody to the monomethyl auristatin E bonded to the linker L-Z—X of formula (V).

13. The antibody-drug conjugate according to claim 2, wherein m is 0.

14. The antibody-drug conjugate according to claim 1, wherein L is a linker molecule of formula (IV):

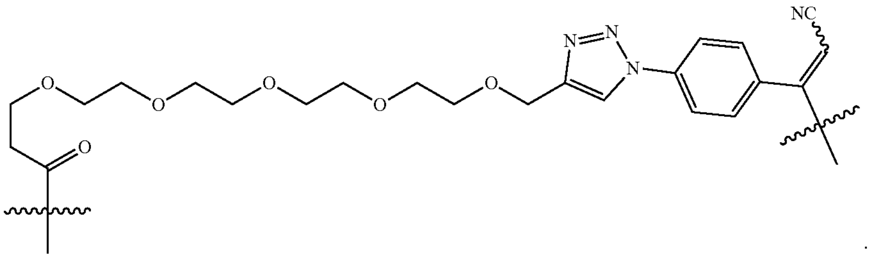 [SMILES: *C(=O)CCOCCOCCOCCOCCOCc1cn(-c2ccc(C(*)=CC#N)cc2)nn1]

15. The antibody-drug conjugate according to claim 1, wherein said antibody is mAb1 comprising a heavy chain of SEQ ID NO:18 and a light chain of SEQ ID NO: 17.

16. A method for treating a tumor according to claim 8, wherein said tumor is a solid tumor or a hematologic tumor.

17. A method for treating a tumor according to claim 8, wherein said tumor is a lymphoma or leukaemia.

18. The antibody-drug conjugate according to claim 1, wherein

Ab is an anti-TfR antibody comprising a heavy chain of SEQ ID NO:18 and a light chain of SEQ ID NO:17, L is a linker molecule bonded to said anti-TfR antibody, said linker molecule being of formula (IV):

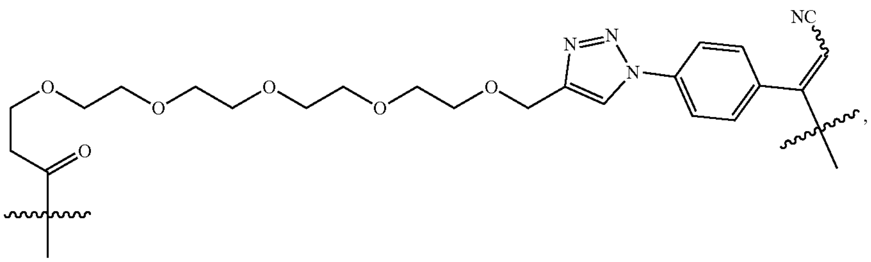 [SMILES: *C(=O)CCOCCOCCOCCOCCOCc1cn(-c2ccc(C(*)=CC#N)cc2)nn1]

Z is a dipeptide of valine-citrulline bonded to L,
X is an aminobenzyl ester self-immolative group bonded to Z, said X being of the following formula (III):
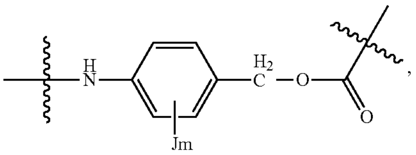
J being an optional substituent chosen among F, Cl, Br, $NO_2$, $NHCOCH_3$, $N(CH_3)_2$, $NHCOCF_3$, alkyl, and haloalkyl, and m being an integer of 0,
D is a drug monomethyl auristatin E bonded to X.
* * * * *